(12) United States Patent
Michaelides et al.

(10) Patent No.: US 8,124,759 B2
(45) Date of Patent: Feb. 28, 2012

(54) INHIBITORS OF PROTEIN KINASES

(75) Inventors: Michael R. Michaelides, Libertyville, IL (US); Zhiqin Ji, Libertyville, IL (US)

(73) Assignee: Abbott Laboratories, Abbott Park, IL (US)

( * ) Notice: Subject to any disclaimer, the term of this patent is extended or adjusted under 35 U.S.C. 154(b) by 957 days.

(21) Appl. No.: 12/118,029

(22) Filed: May 9, 2008

(65) Prior Publication Data

US 2009/0131425 A1    May 21, 2009

Related U.S. Application Data

(60) Provisional application No. 60/916,835, filed on May 9, 2007.

(51) Int. Cl.
| | |
|---|---|
| C07D 487/04 | (2006.01) |
| C07D 401/06 | (2006.01) |
| A61K 31/53 | (2006.01) |
| A61K 31/4412 | (2006.01) |
| A61K 31/4427 | (2006.01) |
| A61P 19/02 | (2006.01) |
| A61P 35/00 | (2006.01) |

(52) U.S. Cl. .................................. 544/183; 514/243
(58) Field of Classification Search ............... 544/183; 514/243

See application file for complete search history.

(56) References Cited

U.S. PATENT DOCUMENTS

| 7,202,363 B2 | 4/2007 | Betschmann et al. |
| 7,514,435 B2 * | 4/2009 | Chen et al. ............ 514/243 |
| 2005/0159427 A1 | 7/2005 | Bruncko et al. |
| 2007/0135387 A1 | 6/2007 | Michaelides et al. |
| 2007/0155776 A1 | 7/2007 | Betschmann et al. |
| 2007/0203143 A1 | 8/2007 | Sheppard et al. |
| 2009/0023743 A1 | 1/2009 | Michaelides et al. |

FOREIGN PATENT DOCUMENTS

| WO | 2005037836 A2 | 4/2005 |
| WO | 2005097800 A1 | 10/2005 |
| WO | 2007041712 A1 | 4/2007 |
| WO | 2007061737 A2 | 5/2007 |
| WO | 2007061882 A2 | 6/2007 |
| WO | 2007064993 A2 | 6/2007 |
| WO | 2007087395 A2 | 8/2007 |
| WO | 2007106503 A2 | 9/2007 |
| WO | 2008089105 A1 | 7/2008 |
| WO | 2008141145 A1 | 11/2008 |

OTHER PUBLICATIONS

Mass, R. D., Int. J. Radiation Oncology Bio. Phys.vol. 58(3): 932-940, 2004.*
Fabbro et al. Pharmacology & therapeutics 93, 79-98, 2002.*
Cohen et al., Current Opinion in Chemical Biology, 3,459-465, 1999.*
Freshney et al.,Culture of Animal Cells, A Manual of Basic Technique, Alan R. Liss, Inc., 1983, New York, p. 4.*
Dermer et al., Bio/Technology, 1994, 12:320.*
Powell et al., British Journal of Dermatology, 141" 802-810, 1999.*
Golub et al., Science, 286, 531-537, 1999.*
Cecil Textbook of Medicine, edited by Bennet, J.C., and Plum F., 20th edition,vol. 1, 1004-1010, 1996.*
Amundson et al., "An Informatics Approach Identifying Markers of Chemosensitivity in Human Cancer Cell Lines," Cancer Research, 60:3101-3110 (2000).
Ghosez et al., "Studies of palladium-catalyzed coupling reactions for preparation of hindered 3-arylpyrroles relevant to (−)rhazinilam and its analogues," Can. J. Chem., 79:1827-1839 (2001).
Holzelova et al., "Autoimmune Lymphoproliferative Syndrome with Somatic Fas Mutations," NEJM, 351:1409-18 (2004).
Keen et al., "Aurora-Kinase Inhibitors as Anti-Cancer Agents," Nature Reviews/Cancer, 4:927-936 (2004).
Puck et al., "Immune Disorders Caused by Defects in the Caspase Cascade," Current Allergy and Asthma Reports, 3:378-384 (2003).
Rengan et al., "Actin cytoskeletal function is spared, but apoptosis is increased, in WAS patient heatopoietic cells," Blood, 95:1283-1292 (2000).
Shimazaki et al., "Evaluation of apoptosis as a prognostic factor in myelodysplastic syndromes," Br. J. of Haematology, 110:584-590 (2000).
The International Search Report, PCT/US2008/063189, Aug. 14, 2008.
Co-pending U.S. Appl. No. 11/636,189, filed Dec. 8, 2006.
Co-pending U.S. Appl. No. 11/617,398, filed Dec. 28, 2006.
Co-pending U.S. Appl. No. 11/675,183, filed Feb. 15, 2007.
Co-pending U.S. Appl. No. 12/118,023, filed May 9, 2008.

* cited by examiner

*Primary Examiner* — Venkataraman Balasubramanian
(74) *Attorney, Agent, or Firm* — Susan L. Steele; Gregory W. Steele

(57) ABSTRACT

Compounds that inhibit Aurora-kinases, compositions containing the compounds and methods of treating diseases using the compounds are disclosed.

9 Claims, No Drawings

INHIBITORS OF PROTEIN KINASES

CROSS-REFERENCE SECTION TO RELATED APPLICATIONS

This application claims priority to U.S. Provisional Application Ser. No. 60/916,835, filed May 9, 2007.

FIELD OF THE INVENTION

This invention pertains to compounds that inhibit protein kinases such as Aurora-kinases, compositions containing the compounds and methods of treating diseases using the compounds.

BACKGROUND OF THE INVENTION

Mitosis is a process by which a complete copy of a duplicated genome is segregated by the microtuble spindle apparatus into two daughter cells. Aurora-kinases, key mitotic regulators required for genome stability, have been found to be overexpressed in human tumors. There is therefore an existing need in the therapeutic arts for compounds, which inhibit Aurora-kinases, compositions comprising the inhibitors and methods of treating diseases during which Aurora-kinases are unregulated or overexpressed.

SUMMARY OF THE INVENTION

One embodiment of this invention, therefore, pertains to compounds that inhibit Aurora-kinases, the compounds having Formula I

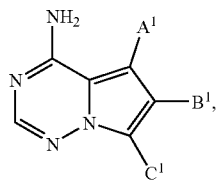

(I)

and therapeutically acceptable salts thereof, wherein $A^1$ is $C(O)NHR^1$, $C(O)N(R^1)_2$, $NHC(O)R^1$, $NR^1C(O)R^1$, $NHC(O)NHR^1$, $NHC(O)N(R^1)_2$, $NR^1C(O)NHR^1$, $NR^1C(O)N(R^1)_2$, $SO_2NHR^1$, $SO_2N(R^1)_2$, $NHSO_2R^1$, $NR^1SO_2R^1$, $OC(O)OR^1$, $NHC(O)OR^1$, $NR^1C(O)OR^1$ or $R^5$;

$B^1$ and $C^1$ are independently H, $R^1$, $C(O)NHR^1$, $C(O)N(R^1)_2$, $NHC(O)R^1$, $NR^1C(O)R^{11}$, $NHC(O)NHR^1$, $NHC(O)N(R^1)_2$, $NR^1C(O)NHR^1$, $NR^1C(O)N(R^1)_2$, $SO_2NHR^1$, $SO_2N(R^1)_2$, $NHSO_2R^1$, $NR^1SO_2R^1$, $OC(O)OR^1$, $NHC(O)OR^1$, $NR^1C(O)OR^1$ or $R^5$; wherein $R^1$ is $R^2$, $R^3$ or $R^4$;

$R^2$ is phenyl, which is unfused or fused with benzene, heteroarene or $R^{2A}$; $R^{2A}$ is cycloalkane, cycloalkene, heterocycloalkane or heterocycloalkene;

$R^3$ is heteroaryl, which is unfused or fused with benzene, heteroarene or $R^{3A}$; $R^{3A}$ is cycloalkane, cycloalkene, heterocycloalkane or heterocycloalkene;

$R^4$ is cycloalkyl, cycloalkenyl, heterocycloalkyl or heterocycloalkenyl, each of which is unfused or fused with benzene, heteroarene or $R^{4A}$; $R^{4A}$ is cycloalkane, cycloalkene, heterocycloalkane or heterocycloalkene;

$R^5$ is alkyl, alkenyl, or alkynyl, each of which is unsubstituted or substituted with one, two, three, four or five of independently selected $R^6$, $OR^6$, $SR^6$, $S(O)R^6$, $SO_2R^6$, $NH_2$, $NHR^6$, $N(R^6)_2$, $C(O)R^6$, $C(O)NH_2$, $C(O)NHR^6$, $C(O)N(R^6)_2$, $NHC(O)R^6$, $NR^6C(O)R^6$, $NHSO_2R^6$, $NR^6SO_2R^6$, $NHC(O)OR^6$, $NR^6C(O)OR^6$, $SO_2NH_2$, $SO_2NHR^6$, $SO_2N(R^6)_2$, $NHC(O)NH_2$, $NHC(O)R^6$, $NHC(O)N(R^6)_2$, $NR^6C(O)N(R^6)_2$, OH, (O), C(O)OH, CN, $CF_3$, $OCF_3$, $CF_2CF_3$, F, Cl, Br or I;

$R^6$ is $R^7$, $R^8$ or $R^9$;

$R^7$ is phenyl which is unfused or fused with benzene, heteroarene or $R^{7A}$; $R^{7A}$ is cycloalkane, cycloalkene, heterocycloalkane or heterocycloalkene;

$R^8$ is heteroaryl which is unfused or fused with benzene, heteroarene or $R^{8A}$; $R^{8A}$ is cycloalkane, cycloalkene, heterocycloalkane or heterocycloalkene;

$R^9$ is cycloalkyl, cycloalkenyl, heterocycloalkyl or heterocycloalkenyl, each of which is unfused or fused with benzene, heteroarene or $R^{9A}$; $R^{9A}$ is cycloalkane, cycloalkene, heterocycloalkane or heterocycloalkene;

wherein each foregoing cyclic moiety is independently unsubstituted or substituted with one or two or three or four or five of independently selected $R^{30}$, $OR^{30}$, $OCH_2R^{30}$, $SR^{30}$ $S(O)R^{30}$, $SO_2R^{30}$, $C(O)R^{30}$, $CO(O)R^{30}$, $OC(O)R^{30}$, $OC(O)OR^{30}$, $NO_2$, $NH_2$, $NHR^{30}$, $N(R^{30})_2$, $C(O)NH_2$, $C(O)NHR^{30}$, $C(O)N(R^{30})_2$, $NHC(O)R^{30}$, $NHC(O)NHR^{30}$, $NHC(O)N(R^{30})_2$, $NR^{30}C(O)NHR^{30}$, $NR^{30}C(O)N(R^{30})_2$, $C(O)NHOH$, $C(O)NHOR^{30}$, $C(O)NHSO_2R^{30}$, $C(O)NR^{30}SO_2R^{30}$, $SO_2NH_2$, $SO_2NHR^{30}$, $SO_2N(R^{30})_2$, $CF_3$, $CF_2CF_3$, $C(O)H$, $C(O)OH$, $C(N)NH_2$, $C(N)NHR^{30}$, $C(N)N(R^{30})_2$, CNOH, $CNOCH_3$, OH, (O), $N_3$, $CF_3$, $CF_2CF_3$, $OCF_3$, $OCF_2CF_3$, F, Cl, Br or I;

$R^{30}$ is $R^{31}$, $R^{32}$, $R^{33}$ or $R^{34}$ $R^{31}$ is phenyl which is unfused or fused with benzene, heteroarene or $R^{31A}$; $R^{31A}$ is cycloalkane, cycloalkene, heterocycloalkane or heterocycloalkene;

$R^{32}$ is heteroaryl which is unfused or fused with benzene, heteroarene or $R^{32A}$; $R^{32A}$ is cycloalkane, cycloalkene, heterocycloalkane or heterocycloalkene;

$R^{33}$ is cycloalkyl, cycloalkenyl, heterocycloalkyl or heterocycloalkenyl, each of which is unfused or fused with benzene, heteroarene or $R^{33A}$; $R^{33A}$ is cycloalkane, cycloalkene, heterocycloalkane or heterocycloalkene;

$R^{34}$ is alkyl, alkenyl, or alkenyl, each of which is unsubstituted or substituted with one, two, three, four or five of independently selected $R^{35}$, $OR^{35}$, $SR^{35}$, $S(O)R^{35}$, $SO_2R^{35}$, $NH_2$, $NHR^{35}$, $N(R^{35})_2$, $C(O)R^{35}$, $C(O)NH_2$, $C(O)NHR^{35}$, $C(O)N(R^{35})_2$, $NHC(O)R^{35}$, $NR^{35}C(O)R^{35}$, $NHSO_2R^{35}$, $NR^{35}SO_2R^{35}$, $NHC(O)OR^{35}$, $NR^{35}C(O)OR^{35}$, $SO_2NH_2$, $SO_2NHR^{35}$, $SO_2N(R^{35})_2$, $NHC(O)NH_2$, $NHC(O)NHR^{35}$, $NHC(O)N(R^{35})_2$, $NR^{35}C(O)N(R^{35})_2$, OH, (O), C(O)OH, CN, $CF_3$, $OCF_3$, $CF_2CF_3$, F, Cl, Br or I;

$R^{35}$ is $R^{36}$, $R^{37}$, $R^{38}$ or $R^{39}$;

$R^{36}$ is phenyl which is unfused or fused with benzene, heteroarene or $R^{36A}$; $R^{36A}$ is cycloalkane, cycloalkene, heterocycloalkane or heterocycloalkene;

$R^{37}$ is heteroaryl which is unfused or fused with benzene, heteroarene or $R^{37A}$; $R^{37A}$ is cycloalkane, cycloalkene, heterocycloalkane or heterocycloalkene;

$R^{38}$ is cycloalkyl, cycloalkenyl, heterocycloalkyl or heterocycloalkenyl, each of which is unfused or fused with benzene, heteroarene or $R^{38A}$; $R^{38A}$ is cycloalkane, cycloalkene, heterocycloalkane or heterocycloalkene;

$R^{39}$ is alkyl, alkenyl or alkenyl, each of which is unsubstituted or substituted with $R^{40}$;

$R^{40}$ is phenyl, heteroaryl, cycloalkyl, cycloalkenyl or heterocycloalkyl;

wherein the moieties represented by $R^{31}$, $R^{32}$, $R^{33}$ $R^{36}$, $R^{37}$ and $R^{38}$ are independently unsubstituted or substituted with one or two or three of independently selected F, Cl, Br, I, OH, (O)OH, $NO_2$, $NH_2$, $CF_3$, $OCF_2$, OH, $R^{45}$, $OR^{45}$, $SR^{45}$, S(O)

$R^{45}$, $SO_2R^{45}$, $C(O)NHR^{45}$, $C(O)N(R^{45})_2$, $NHC(O)R^{45}$, $NR^{45}C(O)R^{45}$, $NHC(O)NHR^{45}$, $NHC(O)N(R^{45})_2$, $NR^{45}C(O)NHR^{45}$, $NR^{45}C(O)N(R^{45})_2$, $SO_2NHR^{45}$, $SO_2N(R^{45})_2$, $NHSO_2R^{45}$, $NR^{45}R^{45}$, $OC(O)OR^{45}$, $NHC(O)OR^{45}$ or $NR^{45}C(O)OR^{45}$;

$R^{45}$ is alkyl, alkenyl or alkynyl, each of which is unsubstituted or substituted with one or two or three of independently selected $R^{50}$, F, Cl, Br, I, OH, C(O)OH, $NO_2$ or $NH_2$; and $R^{50}$ is phenyl, heteroaryl, cycloalkyl, cycloalkenyl or heterocycloalkyl.

Still another embodiment pertains to compositions comprising an excipient and a therapeutically effective amount of a compound having Formula I.

Still another embodiment pertains to methods of treating diseases involving overexpression or unregulation of Aurora-kinases in a mammal, the methods comprising administering thereto a therapeutically effective amount of a compound having Formula I,

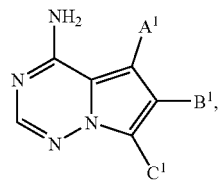

(I)

or a therapeutically acceptable salt thereof, wherein $A^1$ is $C(O)NHR^1$, $C(O)N(R^1)_2$, $NHC(O)R^1$, $NR^1C(O)R^1$, $NHC(O)NHR^1$, $NHC(O)N(R^1)_2$, $NR^1C(O)NHR^1$, $NR^1C(O)N(R^1)_2$, $SO_2NHR_1$, $SO_2N(R^1)_2$, $NHSO_2R^1$, $NR^1SO_2R^1$, $OC(O)OR^1$, $NHC(O)OR^1$, $NR^1C(O)OR^1$ or $R^5$;

$B^1$ and $C^1$ are independently H, $R^1$, $C(O)NHR^1$, $C(O)N(R^1)_2$, $NHC(O)R^1$, $NR^1C(O)R^1$, $NHC(O)NHR^1$, $NHC(O)N(R^1)_2$, $NR^1C(O)NHR^1$, $NR^1C(O)N(R^1)_2$, $SO_2NHR^1$, $SO_2N(R^1)_2$, $NHSO_2R^1$, $NR^1SO_2R^1$, $OC(O)OR^1$, $NHC(O)OR^1$, $NR^1C(O)OR^1$ or $R^5$; wherein $R^1$ is $R^2$, $R^3$ or $R^4$;

$R^2$ is phenyl which is unfused or fused with benzene, heteroarene or $R^{2A}$; $R^{2A}$ is cycloalkane, cycloalkene, heterocycloalkane or heterocycloalkene;

$R^3$ is heteroaryl which is unfused or fused with benzene, heteroarene or $R^{3A}$; $R^{3A}$ is cycloalkane, cycloalkene, heterocycloalkane or heterocycloalkene;

$R^4$ is cycloalkyl, cycloalkenyl, heterocycloalkyl or heterocycloalkenyl, each of which is unfused or fused with benzene, heteroarene or $R^{4A}$; $R^{4A}$ is cycloalkane, cycloalkene, heterocycloalkane or heterocycloalkene;

$R^5$ is alkyl, alkenyl, or alkynyl, each of which is unsubstituted or substituted with one, two, three, four or five of independently selected $R^6$, $OR^6$, $SR^6$, $S(O)R^6$, $SO_2R^6$, $NH_2$, $NHR^6$, $N(R^6)_2$, $C(O)R^6$, $C(O)NH_2$, $C(O)NHR^6$, $C(O)N(R^6)_2$, $NHC(O)R^6$, $NR^6C(O)R^6$, $NHSO_2R^6$, $NR^6SO_2R^6$, $NHC(O)OR^6$, $NR^6C(O)OR^6$, $SO_2NH_2$, $SO_2NHR^6$, $SO_2N(R^6)_2$, $NHC(O)NH_2$, $NHC(O)R^6$, $NHC(O)N(R^6)_2$, $NR^6C(O)N(R^6)_2$, OH, (O), C(O)OH, CN, $CF_3$, $OCF_3$, $CF_2CF_3$, F, Cl, Br or I;

$R^6$ is $R^7$, $R^8$ or $R^9$;

$R^7$ is phenyl which is unfused or fused with benzene, heteroarene or $R^{7A}$; $R^{7A}$ is cycloalkane, cycloalkene, heterocycloalkane or heterocycloalkene;

$R^8$ is heteroaryl which is unfused or fused with benzene, heteroarene or $R^{8A}$; $R^{8A}$ is cycloalkane, cycloalkene, heterocycloalkane or heterocycloalkene;

$R^9$ is cycloalkyl, cycloalkenyl, heterocycloalkyl or heterocycloalkenyl, each of which is unfused or fused with benzene, heteroarene or $R^{9A}$; $R^{9A}$ is cycloalkane, cycloalkene, heterocycloalkane or heterocycloalkene;

wherein each foregoing cyclic moiety is independently unsubstituted or substituted with one or two or three or four or five of independently selected $R^{30}$, $OR^{30}$, $OCH_2R^{30}$, $SR^{30}S(O)R^{30}$, $SO_2R^{30}$, $C(O)R^{30}$, $CO(O)R^{30}$, $OC(O)R^{30}$, $OC(O)OR^{30}$, $NO_2$, $NH_2$, $NHR^{30}$, $N(R^{30})_2$, $C(O)NH_2$, $C(O)NHR^{30}$, $C(O)N(R^{30})_2$, $NHC(O)R^{30}$, $NHC(O)NHR^{30}$, $NHC(O)N(R^3)_2$, $NR^{30}C(O)NHR^{30}$, $NR^{30}C(O)N(R^{30})_2$, $C(O)NHOH$, $C(O)NHOR^{30}$, $C(O)NHSO_2R^{30}$, $C(O)NR^{30}SO_2R^{30}$, $SO_2NH_2$, $SO_2NHR^{30}$, $SO_2N(R^{30})_2$, $CF_3$, $CF_2CF_3$, $C(O)H$, C(O)OH, $C(N)NH_2$, $C(N)NHR^{30}$, $C(N)N(R^{30})_2$, CNOH, $CNOCH_3$, OH, (O), $N_3$, $CF_3$, $CF_2CF_3$, $OCF_3$, $OCF_2CF_3$, F, Cl, Br or I;

$R^{30}$ is $R^{31}$, $R^{32}$, $R^{33}$ or $R^{34}$;

$R^{31}$ is phenyl which is unfused or fused with benzene, heteroarene or $R^{31A}$; $R^{31A}$ is cycloalkane, cycloalkene, heterocycloalkane or heterocycloalkene;

$R^{32}$ is heteroaryl which is unfused or fused with benzene, heteroarene or $R^{32A}$; $R^{32A}$ is cycloalkane, cycloalkene, heterocycloalkane or heterocycloalkene;

$R^{33}$ is cycloalkyl, cycloalkenyl, heterocycloalkyl or heterocycloalkenyl, each of which is unfused or fused with benzene, heteroarene or $R^{33A}$; $R^{33A}$ is cycloalkane, cycloalkene, heterocycloalkane or heterocycloalkene;

$R^{34}$ is alkyl, alkenyl, or alkenyl, each of which is unsubstituted or substituted with one, two, three, four or five of independently selected $R^{35}$, $OR^{35}$, $SR^{35}$, $S(O)R^{35}$, $SO_2R^{35}$, $NH_2$, $NHR^{35}$, $N(R^{35})_2$, $C(O)R^{35}$, $C(O)NH_2$, $C(O)NHR^{35}$, $C(O)N(R^{35})_2$, $NHC(O)R^{35}$, $NR^{35}C(O)R^{35}$, $NHSO_2R^{35}$, $NR^{35}SO_2R^{35}$, $NHC(O)OR^{35}$, $NR^{35}C(O)OR^{35}$, $S_2NH_2$, $SO_2NHR^{35}$, $SO_2N(R^{35})_2$, $NHC(O)NH_2$, $NHC(O)NHR^{35}$, $NHC(O)N(R^{35})_2$, $NR^{35}C(O)N(R^{35})_2$, OH, (O), C(O)OH, CN, $CF_3$, $OCF_3$, $CF_2CF_3$, F, Cl, Br or I;

$R^{35}$ is $R^{36}$, $R^{37}$, $R^{38}$ or $R^{39}$;

$R^{36}$ is phenyl which is unfused or fused with benzene, heteroarene or $R^{36A}$; $R^{36A}$ is cycloalkane, cycloalkene, heterocycloalkane or heterocycloalkene;

$R^{37}$ is heteroaryl which is unfused or fused with benzene, heteroarene or $R^{37A}$; $R^{37A}$ is cycloalkane, cycloalkene, heterocycloalkane or heterocycloalkene;

$R^{38}$ is cycloalkyl, cycloalkenyl, heterocycloalkyl or heterocycloalkenyl, each of which is unfused or fused with benzene, heteroarene or $R^{38A}$; $R^{38A}$ is cycloalkane, cycloalkene, heterocycloalkane or heterocycloalkene;

$R^{39}$ is alkyl, alkenyl or alkenyl, each of which is unsubstituted or substituted with $R^{40}$;

$R^{40}$ is phenyl, heteroaryl, cycloalkyl, cycloalkenyl or heterocycloalkyl;

wherein the moieties represented by $R^{31}$, $R^{32}$, $R^{33}R^{36}$, $R^{37}$ and $R^{38}$ are independently unsubstituted or substituted with one or two or three of independently selected F, Cl, Br, I, OH, (O)OH, $NO_2$, $NH_2$, $CF_3$, $OCF_2$, OH, $R^{45}$, $OR^{45}$, $SR^{45}$, $S(O)R^{45}$, $SO_2R^{45}$, $C(O)NHR^{45}$, $C(O)N(R^{45})_2$, $NHC(O)R^{45}$, $NR^{45}C(O)R^{45}$, $NHC(O)NHR^{45}$, $NHC(O)N(R^{45})_2$, $NR^{45}C(O)NHR^{45}$, $NR^{45}C(O)N(R^{45})_2$, $SO_2NHR^{45}$, $SO_2N(R^{45})_2$, $NHSO_2R^{45}$, $NR^1SO_2R^{45}$, $OC(O)OR^{45}$, $NHC(O)OR^{45}$ or $NR^{45}C(O)OR^{45}$;

$R^{45}$ is alkyl, alkenyl or alkynyl, each of which is unsubstituted or substituted with one or two or three of independently selected $R^{50}$, F, Cl, Br, I, OH, C(O)OH, $NO_2$ or $NH_2$; and $R^{50}$ is phenyl, heteroaryl, cycloalkyl, cycloalkenyl or heterocycloalkyl, with or without also administering radiotherapy thereto.

Still another embodiment pertains to methods of treating bladder cancer, breast cancer, cervical cancer, colon cancer, endometrial cancer, esophageal cancer, lung cancer, ovarian cancer, pancreatic cancer, prostate cancer, rectal cancer, skin cancer, stomach cancer and thyroid cancer in a mammal, the methods comprising administering thereto a therapeutically effective amount of a compound having Formula I, with or without also administering radiotherapy thereto.

Still another embodiment pertains to compositions comprising an excipient and a therapeutically effective amount of a compound having Formula I and a therapeutically effective amount of one additional therapeutic agent or more than one additional therapeutic agent.

Still another embodiment pertains to methods of treating diseases involving overexpression or unregulation of Aurora-kinases in a mammal, the methods comprising administering thereto a therapeutically effective amount of a compound having Formula I and a therapeutically effective amount of one additional therapeutic agent or more than one additional therapeutic agent with or without also administering radiotherapy thereto.

Still another embodiment pertains to methods of treating bladder cancer, breast cancer, cervical cancer, colon cancer, endometrial cancer, esophageal cancer, lung cancer, ovarian cancer, pancreatic cancer, prostate cancer, rectal cancer, skin cancer, stomach cancer and thyroid cancer in a mammal, the methods comprising administering thereto a therapeutically effective amount of a compound having Formula I and a therapeutically effective amount of one additional therapeutic agent or more than one additional therapeutic agent, with or without also administering radiotherapy thereto.

Still another embodiment pertains to compounds 4-amino-N-(4-((((3-fluorophenyl)amino)carbonyl)amino)phenyl)pyrrolo[2,1-f][2,1,4]triazine-5-carboxamide, 4-amino-N-(4-((((4-fluorophenyl)amino)carbonyl)amino)phenyl)pyrrolo[2,1-f][2,1,4]triazine-5-carboxamide, 4-amino-N-(4-((((2-fluorophenyl)amino)carbonyl)amino)phenyl)pyrrolo[2,1-f][2,1,4]triazine-5-carboxamide, 4-amino-N-(4-((anilinocarbonyl)amino)phenyl)pyrrolo[2,1-f][2,1,4]triazine-5-carboxamide, 4-amino-N-(4-((((3,5-dimethylphenyl)amino)carbonyl)amino)phenyl)pyrrolo[2,1-f][2,1,4]triazine-5-carboxamide, 4-amino-N-(4-((((3-methylphenyl)amino)carbonyl)amino)phenyl)pyrrolo[2,1-f][2,1,4]triazine-5-carboxamide, 4-amino-N-(4-((((4-methylphenyl)amino)carbonyl)amino)phenyl)pyrrolo[2,1-f][2,1,4]triazine-5-carboxamide, 4-amino-N-(4-((((2-methylphenyl)amino)carbonyl)amino)phenyl)pyrrolo[2,1-f][2,1,4]triazine-5-carboxamide, 4-amino-N-(4-((((3-methoxyphenyl)amino)carbonyl)amino)phenyl)pyrrolo[2,1-f][2,1,4]triazine-5-carboxamide, 4-amino-N-(4-((((4-methoxyphenyl)amino)carbonyl)amino)phenyl)pyrrolo[2,1-f][2,1,4]triazine-5-carboxamide, 4-amino-N-(4-((((3-(trifluoromethyl)phenyl)amino)carbonyl)amino)phenyl)pyrrolo[2,1-f][2,1,4]triazine-5-carboxamide, 4-amino-N-(4-(((cyclopropylamino)carbonyl)amino)phenyl)pyrrolo[2,1-f][2,1,4]triazine-5-carboxamide, 4-amino-N-(4-(((cyclopentylamino)carbonyl)amino)phenyl)pyrrolo[2,1-f][2,1,4]triazine-5-carboxamide, 4-amino-N-(4-(((thien-3-ylamino)carbonyl)amino)phenyl)pyrrolo[2,1-f][2,1,4]triazine-5-carboxamide, 4-amino-N-(4-(((pyridin-3-ylamino)carbonyl)amino)phenyl)pyrrolo[2,1-f][2,1,4]triazine-5-carboxamide, 4-amino-N-(4-(benzoylamino)phenyl)pyrrolo[2,1-f][2,1,4]triazine-5-carboxamide, 4-amino-N-(4-((((2-fluoro-5-methylphenyl)amino)carbonyl)amino)phenyl)pyrrolo[2,1-f][2,1,4]triazine-5-carboxamide, 4-amino-N-(4-(((((4-(2-hydroxyethyl)phenyl)amino)carbonyl)amino)phenyl)pyrrolo[2,1-f][2,1,4]triazine-5-carboxamide, 4-amino-N-(4-(((((3-(2-hydroxyethyl)phenyl)amino)carbonyl)amino)phenyl)pyrrolo[2,1-f][2,1,4]triazine-5-carboxamide, 4-amino-N-(4-(((((3-(hydroxymethyl)phenyl)amino)carbonyl)amino)phenyl)pyrrolo[2,1-f][2,1,4]triazine-5-carboxamide, 4-amino-N-(4-(((((3-(3-hydroxypropoxy)phenyl)amino)carbonyl)amino)phenyl)pyrrolo[2,1-f][2,1,4]triazine-5-carboxamide, 4-amino-N-(3-((anilinocarbonyl)amino)phenyl)pyrrolo[2,1-f][2,1,4]triazine-5-carboxamide, 4-amino-N-(3-((((3-methylphenyl)amino)carbonyl)amino)phenyl)pyrrolo[2,1-f][2,1,4]triazine-5-carboxamide, 4-amino-N-(5-(2-(((3-fluorophenyl)amino)-2-oxoethyl)-1,3-thiazol-2-yl)pyrrolo[2,1-f][2,1,4]triazine-5-carboxamide, 4-amino-N-(4-(((((3-(morpholin-4-ylmethyl)phenyl)amino)carbonyl)amino)phenyl)pyrrolo[2,1-f][2,1,4]triazine-5-carboxamide, 4-amino-N-(4-(((((3-methylphenyl)amino)carbonyl)amino)methyl)phenyl)pyrrolo[2,1-f][2,1,4]triazine-5-carboxamide, 4-amino-N-(4-(((((3-fluorophenyl)amino)carbonyl)amino)methyl)phenyl)pyrrolo[2,1-f][2,1,4]triazine-5-carboxamide, 4-amino-N-(3-(((((3-fluorophenyl)amino)carbonyl)amino)methyl)phenyl)pyrrolo[2,1-f][2,1,4]triazine-5-carboxamide, 4-amino-N-(3-(((anilinocarbonyl)amino)methyl)phenyl)pyrrolo[2,1-f][2,1,4]triazine-5-carboxamide 4-amino-N-(3-(((((4-(trifluoromethyl)phenyl)amino)carbonyl)amino)methyl)phenyl)pyrrolo[2,1-f][2,1,4]triazine-5-carboxamide;

4-amino-N-(3-(((((3,4-difluorophenyl)amino)carbonyl)amino)methyl)phenyl)pyrrolo[2,1-f][2,1,4]triazine-5-carboxamide;

4-amino-N-(3-(((((4-chloro-2-fluorophenyl)amino)carbonyl)amino)methyl)phenyl)pyrrolo[2,1-f][2,1,4]triazine-5-carboxamide;

4-amino-N-(3-(((((3-chlorophenyl)amino)carbonyl)amino)methyl)phenyl)pyrrolo[2,1-f][2,1,4]triazine-5-carboxamide;

4-amino-N-(3-(((((4-methylphenyl)amino)carbonyl)amino)methyl)phenyl)pyrrolo[2,1-f][2,1,4]triazine-5-carboxamide;

4-amino-N-(3-(((((4-chlorophenyl)amino)carbonyl)amino)methyl)phenyl)pyrrolo[2,1-f][2,1,4]triazine-5-carboxamide;

4-amino-N-(3-(((((4-fluorophenyl)amino)carbonyl)amino)methyl)phenyl)pyrrolo[2,1-f][2,1,4]triazine-5-carboxamide;

4-amino-N-(3-((((pyridin-3-ylamino)carbonyl)amino)methyl)phenyl)pyrrolo[2,1-f][2,1,4]triazine-5-carboxamide;

4-amino-N-(3-(((((4-(difluoromethoxy)phenyl)amino)carbonyl)amino)methyl)phenyl)pyrrolo[2,1-f][2,1,4]triazine-5-carboxamide;

4-amino-N-(3-(((((2,4-difluorophenyl)amino)carbonyl)amino)methyl)phenyl)pyrrolo[2,1-f][2,1,4]triazine-5-carboxamide;

4-amino-N-(3-(((((2,5-difluorophenyl)amino)carbonyl)amino)methyl)phenyl)pyrrolo[2,1-f][2,1,4]triazine-5-carboxamide;

4-amino-N-(4-(((((4-chloro-2-fluorophenyl)amino)carbonyl)amino)phenyl)pyrrolo[2,1-f][2,1,4]triazine-5-carboxamide;

4-amino-N-(4-((((4-(trifluoromethyl)phenyl)amino)carbonyl)amino)phenyl)pyrrolo[2,1-f][2,1,4]triazine-5-carboxamide;

and therapeutically acceptable salts, prodrugs, esters, amides, salts of prodrugs, salts of esters, and salts of amides thereof.

DETAILED DESCRIPTION OF THE INVENTION

Variable moieties of compounds herein are represented by identifiers (capital letters with numerical and/or alphabetical superscripts) and may be specifically embodied.

It is meant to be understood that proper valences are maintained for all moieties and combinations thereof, that monovalent moieties having more than one atom are attached through their left ends.

It is also meant to be understood that a specific embodiment of a variable moiety may be the same or different as another specific embodiment having the same identifier.

The term "cyclic moiety," as used herein, means benzene, cycloalkane, cycloalkyl, cycloalkene, cycloalkenyl, heteroarene, heteroaryl, heterocycloalkane, heterocycloalkyl, heterocycloalkene, heterocycloalkenyl and phenyl.

The term "cycloalkane," as used herein, means $C_3$-cycloalkane, $C_4$-cycloalkane, $C_5$-cycloalkane and $C_6$-cycloalkane.

The term "cycloalkyl," as used herein, means $C_3$-cycloalkyl, $C_4$-cycloalkyl, $C_5$-cycloalkyl and $C_6$-cycloalkyl.

The term "cycloalkene," as used herein, means $C_4$-cycloalkene, $C_5$-cycloalkene and $C_6$-cycloalkene.

The term "cycloalkenyl," as used herein, means $C_4$-cycloalkenyl, $C_5$-cycloalkenyl and $C_6$-cycloalkenyl.

The term "heteroarene," as used herein, means furan, imidazole, isothiazole, isoxazole, 1,2,3-oxadiazole, 1,2,5-oxadiazole, oxazole, pyrazine, pyrazole, pyridazine, pyridine, pyrimidine, pyrrole, thiazole, thiophene, triazine and 1,2,3-triazole.

The term "heteroaryl," as used herein, means furanyl, imidazolyl, isothiazolyl, isoxazolyl, 1,2,3-oxadiazoyl, 1,2,5-oxadiazolyl, oxazolyl, pyrazinyl, pyrazolyl, pyridazinyl, pyridinyl, pyrimidinyl, pyrrolyl, tetrazolyl, thiazolyl, thiophenyl, triazinyl and 1,2,3-triazolyl.

The term "heterocycloalkane," as used herein, means cycloalkane having one or two or three $CH_2$ moieties replaced with independently selected O, S, S(O), $SO_2$ or NH and one or two CH moieties unreplaced or replaced with N and also means cycloalkane having one or two or three $CH_2$ moieties unreplaced or replaced with independently selected O, S, S(O), $SO_2$ or NH and one or two CH moieties replaced with N.

The term "heterocycloalkyl," as used herein, means cycloalkyl having one or two or three $CH_2$ moieties replaced with independently selected O, S, S(O), $SO_2$ or NH and one or two CH moieties unreplaced or replaced with N and also means cycloalkyl having one or two or three $CH_2$ moieties unreplaced or replaced with independently selected O, S, S(O), $SO_2$ or NH and one or two CH moieties replaced with N.

The term "heterocycloalkene," as used herein, means cycloalkene having one or two or three $CH_2$ moieties replaced with independently selected O, S, S(O), $SO_2$ or NH and one or two CH moieties unreplaced or replaced with N and also means cycloalkene having one or two or three $CH_2$ moieties unreplaced or replaced with independently selected O, S, S(O), $SO_2$ or NH and one or two CH moieties replaced with N.

The term "heterocycloalkenyl," as used herein, means cycloalkenyl having one or two or three $CH_2$ moieties replaced with independently selected O, S, S(O), $SO_2$ or NH and one or two CH moieties unreplaced or replaced with N and also means cycloalkenyl having one or two or three $CH_2$ moieties unreplaced or replaced with independently selected O, S, S(O), $SO_2$ or NH and one or two CH moieties replaced with N.

The term "alkenyl," as used herein, means $C_2$-alkenyl, $C_3$-alkenyl, $C_4$-alkenyl, $C_5$-alkenyl and $C_6$-alkenyl.

The term "alkyl," as used herein, means $C_1$-alkyl, $C_2$-alkyl, $C_3$-alkyl, $C_4$-alkyl, $C_5$-alkyl and $C_6$-alkyl.

The term "alkynyl," as used herein, means $C_2$-alkynyl, $C_3$-alkynyl, $C_4$-alkynyl, $C_5$-alkynyl and $C_6$-alkynyl.

Compounds of this invention may contain asymmetrically substituted carbon atoms in the R or S configuration, wherein the terms "R" and "S" are as defined in Pure Appl. Chem. (1976) 45, 13-10. Compounds having asymmetrically substituted carbon atoms with equal amounts of R and S configurations are racemic at those atoms. Atoms having excess of one configuration over the other are assigned the configuration in excess, preferably an excess of about 85%-90%, more preferably an excess of about 95%-99%, and still more preferably an excess greater than about 99%. Accordingly, this invention is meant to embrace racemic mixtures and relative and absolute diastereoisomers of the compounds thereof.

Compounds of this invention may also contain carbon-carbon double bonds or carbon-nitrogen double bonds in the Z or E configuration, in which the term "Z" represents the larger two substituents on the same side of a carbon-carbon or carbon-nitrogen double bond and the term "E" represents the larger two substituents on opposite sides of a carbon-carbon or carbon-nitrogen double bond. The compounds of this invention may also exist as a mixture of "Z" and "E" isomers.

Compounds of this invention may also exist as tautomers or equilibrium mixtures thereof wherein a proton of a compound shifts from one atom to another. Examples of tautomers include, but are not limited to, keto-enol, phenol-keto, oxime-nitroso, nitro-acid, imine-enamine and the like.

Compounds of this invention containing NH, C(O)OH, OH or SH moieties may have attached thereto prodrug-forming moieties. The prodrug-forming moieties are removed by metabolic processes and release the compounds having the freed NH, C(O)OH, OH or SH in vivo. Prodrugs are useful for adjusting such pharmacokinetic properties of the compounds as solubility and/or hydrophobicity, absorption in the gastrointestinal tract, bioavailability, tissue penetration, and rate of clearance.

Metabolites of compounds having Formula I produced by in vitro or in vivo metabolic processes, may also have utility for treating diseases associated with overexpression or unregulation of protein kinases.

Certain precursor compounds which may be metabolized in vitro or in vivo to form compounds having Formula I may also have utility for treating diseases associated with overexpression or unregulation of protein kinases.

Compounds having Formula I may exist as acid addition salts, basic addition salts or zwitterions. Salts of compounds having Formula I are prepared during their isolation or following their purification. Acid addition salts are those derived from the reaction of a compound having Formula I with acid. Accordingly, salts including the acetate, adipate, alginate, bicarbonate, citrate, aspartate, benzoate, benzenesulfonate (besylate), bisulfate, butyrate, camphorate, camphorsulfonate, digluconate, formate, fumarate, glycerophosphate, glutamate, hemisulfate, heptanoate, hexanoate, hydrochloride, hydrobromide, hydroiodide, lactobionate, lactate, maleate, mesitylenesulfonate, methanesulfonate, naphthylenesulfonate, nicotinate, oxalate, pamoate, pectinate, persulfate, phosphate, picrate, propionate, succinate, tartrate, thiocyanate, trichloroacetic, trifluoroacetic, para-toluenesulfonate and undecanoate salts of the compounds having Formula I are meant to be embraced by this invention. Basic addition salts of compounds are those derived from the reaction of the compounds having Formula I with the bicarbonate, carbonate, hydroxide or phosphate of cations such as lithium, sodium, potassium, calcium and magnesium.

Compounds having Formula I may be administered, for example, bucally, ophthalmically, orally, osmotically, parenterally (intramuscularly, intraperintoneally intrasternally, intravenously, subcutaneously), rectally, topically, transdermally, vaginally and intraarterially as well as by intraarticular injection, infusion, and placement in the body, such as, for example, the vasculature.

Therapeutically effective amounts of a compound having Formula I depend on recipient of treatment, disease treated and severity thereof, composition comprising it, time of administration, route of administration, duration of treatment, potency, rate of clearance and whether or not another drug is co-administered. The amount of a compound having Formula I used to make a composition to be administered daily to a patient in a single dose or in divided doses is from about 0.03 to about 200 mg/kg body weight. Single dose compositions contain these amounts or a combination of submultiples thereof.

Compounds having Formula I may be administered with or without an excipient. Excipients include, but are not limited to, encapsulators and additives such as absorption accelerators, antioxidants, binders, buffers, coating agents, coloring agents, diluents, disintegrating agents, emulsifiers, extenders, fillers, flavoring agents, humectants, lubricants, perfumes, preservatives, propellants, releasing agents, sterilizing agents, sweeteners, solubilizers, wetting agents, mixtures thereof and the like.

Excipients for preparation of compositions comprising a compound having Formula I to be administered orally include, but are not limited to, agar, alginic acid, aluminum hydroxide, benzyl alcohol, benzyl benzoate, 1,3-butylene glycol, carbomers, castor oil, cellulose, cellulose acetate, cocoa butter, corn starch, corn oil, cottonseed oil, cross-povidone, diglycerides, ethanol, ethyl cellulose, ethyl laureate, ethyl oleate, fatty acid esters, gelatin, germ oil, glucose, glycerol, groundnut oil, hydroxypropylmethyl celluose, isopropanol, isotonic saline, lactose, magnesium hydroxide, magnesium stearate, malt, mannitol, monoglycerides, olive oil, peanut oil, potassium phosphate salts, potato starch, povidone, propylene glycol, Ringer's solution, safflower oil, sesame oil, sodium carboxymethyl cellulose, sodium phosphate salts, sodium lauryl sulfate, sodium sorbitol, soybean oil, stearic acids, stearyl fumarate, sucrose, surfactants, talc, tragacanth, tetrahydrofurfuryl alcohol, triglycerides, water, mixtures thereof and the like. Excipients for preparation of compositions comprising a compound having Formula I to be administered ophthalmically or orally include, but are not limited to, 1,3-butylene glycol, castor oil, corn oil, cottonseed oil, ethanol, fatty acid esters of sorbitan, germ oil, groundnut oil, glycerol, isopropanol, olive oil, polyethylene glycols, propylene glycol, sesame oil, water, mixtures thereof and the like. Excipients for preparation of compositions comprising a compound having Formula I to be administered osmotically include, but are not limited to, chlorofluorohydrocarbons, ethanol, water, mixtures thereof and the like. Excipients for preparation of compositions comprising a compound having Formula I to be administered parenterally include, but are not limited to, 1,3-butanediol, castor oil, corn oil, cottonseed oil, dextrose, germ oil, groundnut oil, liposomes, oleic acid, olive oil, peanut oil, Ringer's solution, safflower oil, sesame oil, soybean oil, U.S.P. or isotonic sodium chloride solution, water, mixtures thereof and the like. Excipients for preparation of compositions comprising a compound having Formula I to be administered rectally or vaginally include, but are not limited to, cocoa butter, polyethylene glycol, wax, mixtures thereof and the like.

Compounds having Formula I are also expected to be useful as chemotherapeutic agents in combination with actinomycins, alkylating agents, anthracyclines, antifolates, antiestrogen agents, anti-metabolites, anti-androgens, antimicrotubule agents, aromatase inhibitors, bleomycins, $Ca^{2+}$ adenosine triphosphate (ATP)ase inhibitors, cytosine analogs, deltoids/retinoids, dihydrofolate reductase inhibitors, deoxyribonucleic acid (DNA) topoisomerase inhibitors, dopaminergic neurotoxins, glucocorticoids, histone deacetylase inhibitors, hormonal therapies, immunotherapeutic agents, inosine monophosphate (IMP) dehydrogenase inhibitors, isoprenylation inhibitors, luteinizing hormone-releasing hormone agonists, mammalian target of rapamycin (mtor) inhibitors, multi-drug resistance (MDR) inhibitors, mitomycins, photodyamic therapies, proteasome inhibitors, platinum containing compounds, radiation, receptor tyrosine kinase inhibitors, ribonucleotide reductase inhibitors, thrombospondin mimetics, uracil analogs, vinca alkaloids, and vitamin D3 analogs such as, but not limited to, $\gamma$-radiation or an additional chemotherapeutic agent or additional chemotherapeutic agents such as N-Ac-Sar-Gly-Val-D-alloIle-Thr-Nva-Ile-Arg-Pro-NHCH$_2$CH$_3$ or a salt thereof, actinomycin D, AG13736, 17-allylamino-17-demethoxygeldanamycin, 9-aminocamptothecin, N-(4-(3-amino-1H-indazol-4-yl)phenyl)-N'-(2-fluoro-5-methylphenyl)urea or a salt thereof, N-(4-(4-aminothieno(2,3-d)pyrimidin-5-yl)phenyl)-N'-(2-fluoro-5-(trifluoromethyl)phenyl)urea or a salt thereof, anastozole, AP-23573, asparaginase, azacitidine, bevacizumab, bicalutamide, bleomycin a2, bleomycin b2, bortezamib, busulfan, campathecins, carboplatin, carmustine (BCNU), CB1093, cetuximab, CHOP (C: Cytoxan® (cyclophosphamide); H: Adriamycin® (hydroxydoxorubicin); O: Vincristine (Oncovin®); P: prednisone), chlorambucil, CHIR258, cisplatin, CNF-101, CNF-1001, CNF-2024, CP547632, crisnatol, cytarabine, cyclophosphamide, cytosine arabinoside, daunorubicin, dacarbazine, dactinomycin, dasatinib, daunorubicin, deferoxamine, demethoxyhypocrellin A, depsipeptide, dexamethasone, 17-dimethylaminoethylamino-17-demethoxygeldanamycin, docetaxel, doxifluridine, doxorubicin, EB1089, epothilone D, epirubicin, 5-ethynyl-1-β-D-ribofuranosylimidazole-4-carboxamide (EICAR), erlotinib, etoposide, everolimus, 5-fluorouracil (5-FU), floxuridine, fludarabine, flutamide, gefitinib, geldanamycin, gemcitabine, goserelin, N-(2-(4-hydroxyanilino)-3-pyridinyl)-4-methoxybenzenesulfonamide or a salt thereof, hydroxyurea, idarubicin, ifosfamide, imatinab, interferon-α, interferon-γ, IPI-504, irinotecan, KH 1060, lapatanib, LAQ824, leuprolide acetate, letrozole, lomustine (CCNU), lovastatin, megestrol, melphalan, mercaptopurine, methotrexate, 1-methyl-4-phyenylpyridinium, MG 132, mitomycin, mitoxantrone, MLN-518, MS-275, mycophenolic acid, mitomycin C, nitrosoureas, oxaliplatin, paclitaxel, PD98059, peplomycin, photosensitizer Pc4, phtalocyanine, pirarubicin, plicamycin, prednisone, procarbizine, PTK787, PU24FC1, PU3, radicicol, raloxifene, rapamycin, ratitrexed, retinoids such as pheuretinide, ribavirin, rituximab (Rituxin®), sorafenib, staurosporine, steroids such as dexamethasone and prednisone, suberoylanilide hydroxamic acid, sunitinib, tamoxifen, taxol, temozolamide, temsirolimus, teniposide, thapsigargin, thioguanine, thrombospondin-1, tiazofurin, topotecan, trapoxin, trastuzumab, treosulfan, trichostatin A, trimetrexate, trofosfamide, tumor necrosis factor, valproic acid, VER49009, verapamil, vertoporfin, vinblastine, vincristine, vindesine, vinorelbine vitamin D3, VX-680, zactima, ZK-EPO, zorubicin or combinations thereof. To determine activity of representative compounds of the invention, Active Aurora B enzyme (recombinant residues 1-344) and INCENP (recombinant GST fusion protein from Upstate) were incubated in wells of a 384 well plate with biotinylated histone H3 peptide residues 1-21 (Upstate), 1 mM ATP, and various concentrations of inhibitors in a Hepes buffer, pH 7.4 containing $MgCl_2$, sodium othrovanadate, and Triton X-100. After 1 hour, the reaction was stopped with EDTA and anti-phospho-histone H3 Europium Cryptate (Cis-Bio) and SA-APC (Phycolink, Prozyme) were added to detect the phosphopeptide. The amount of phosphorylation was determined by the time-resolved fluorescence ratio of signals at 665 nm and 615 nm. The $IC_{50}$'s were calculated by an exponential fit of the inhibition values with the inhibitor concentrations using Assay Explorer software and are shown in TABLE 1.

TABLE 1

| | | | | | |
|---|---|---|---|---|---|
| 0.001 | 0.001 | 0.001 | 0.001 | 0.001 | 0.002 |
| 0.003 | 0.004 | 0.005 | 0.008 | 0.009 | 0.009 |
| 0.012 | 0.012 | 0.013 | 0.016 | 0.017 | 0.022 |
| 0.024 | 0.033 | 0.036 | 0.038 | 0.040 | 0.094 |
| 0.109 | 0.120 | 0.121 | 0.126 | 0.139 | 0.175 |
| 0.194 | 0.302 | 0.370 | 0.446 | 0.930 | 1.170 |
| 1.590 | 2.010 | 2.140 | 5.390 | >12.5 | >12.5 |

These data demonstrate the utility of compounds having Formula I as inhibitors of Aurora-kinase B.

It is expected that, because compounds having Formula I inhibit the activity of Aurora-kinase B, they could also have utility as inhibitors of protein kinases having close structural homology thereto, such as, for example, Aurora-kinase A and Aurora-kinase C.

The structural homology between Protein Kinases A, B and C is reported in Nature Reviews/Cancer, Vol. 4 Dec. 2004.

Accordingly, compounds having Formula I are expected to have utility in treatment of diseases during which protein kinases such as any or all Aurora-kinase family members are expressed.

Diseases involving overexpression or unregulation of Aurora-kinase family members include, but are not limited to, acoustic neuroma, acute leukemia, acute lymphocytic leukemia, acute myelocytic leukemia (monocytic, myeloblastic, adenocarcinoma, angiosarcoma, astrocytoma, myelomonocytic and promyelocytic), acute t-cell leukemia, basal cell carcinoma, bile duct carcinoma, bladder cancer, brain cancer, breast cancer, bronchogenic carcinoma, cervical cancer, chondrosarcoma, chordoma, choriocarcinoma, chronic leukemia, chronic lymphocytic leukemia, chronic myelocytic (granulocytic) leukemia, chronic myleogeneous leukemia, colon cancer, colorectal cancer, craniopharyngioma, cystadenocarcinoma, diffuse large B-cell lymphoma, dysproliferative changes (dysplasias and metaplasias), embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, follicular lymphoma, germ cell testicular cancer, glioma, heavy chain disease, hemangioblastoma, hepatoma, hepatocellular cancer, hormone insensitive prostate cancer, leiomyosarcoma, liposarcoma, lung cancer, lymphagioendotheliosarcoma, lymphangiosarcoma, lymphoblastic leukemia, lymphoma (Hodgkin's and non-Hodgkin's), malignancies and hyperproliferative disorders of the bladder, breast, colon, lung, ovaries, pancreas, prostate, skin and uterus, lymphoid malignancies of T-cell or B-cell origin, leukemia, lymphoma, medullary carcinoma, medulloblastoma, melanoma, meningioma, mesothelioma, multiple myeloma, myelogenous leukemia, myeloma, myxosarcoma, neuroblastoma, non-small cell lung cancer, oligodendroglioma, oral cancer, osteogenic sarcoma, ovarian cancer, pancreatic cancer, papillary adenocarcinomas, papillary carcinoma, pinealoma, polycythemia vera, prostate cancer, rectal cancer, renal cell carcinoma, retinoblastoma, rhabdomyosarcoma, sarcoma, sebaceous gland carcinoma, seminoma, skin cancer, small cell lung carcinoma, solid tumors (carcinomas and sarcomas), small cell lung cancer, stomach cancer, squamous cell carcinoma, synovioma, sweat gland carcinoma, thyroid cancer, Waldenström's macroglobulinemia, testicular tumors, uterine cancer and Wilms' tumor.

It is also expected that compounds having Formula I would inhibit the growth of cells derived from a cancer or neoplasm such as breast cancer (including estrogen-receptor positive breast cancer), colorectal cancer, endometrial cancer, lung cancer (including small cell lung cancer), lymphoma (including follicular or Diffuse Large B-cell), lymphoma (including non-Hodgkin's lymphoma), neuroblastoma, ovarian cancer, prostate cancer (including hormone-insensitive prostate cancer) and testicular cancer (including germ cell testicular cancer).

It is also expected that compounds having Formula I would inhibit the growth of cells derived from a pediatric cancer or neoplasm such as embryonal rhabdomyosarcoma, pediatric acute lymphoblastic leukemia, pediatric acute myelogenous leukemia, pediatric alveolar rhabdomyosarcoma, pediatric anaplastic ependymoma, pediatric anaplastic large cell lymphoma, pediatric anaplastic medulloblastoma, pediatric atypical teratoid/rhabdoid tumor of the central nervous syatem, pediatric biphenotypic acute leukemia, pediatric Burkitts lymphoma, pediatric cancers of Ewing's family of tumors such as primitive neuroectodermal rumors, pediatric diffuse anaplastic Wilm's tumor, pediatric favorable histology Wilm's tumor, pediatric glioblastoma, pediatric medulloblastoma, pediatric neuroblastoma, pediatric neuroblastoma-derived myelocytomatosis, pediatric pre-B-cell cancers (such as leukemia), pediatric psteosarcoma, pediatric rhabdoid kidney tumor, pediatric rhabdomyosarcoma, and pediatric T-cell cancers such as lymphoma and skin cancer.

Compounds having Formula I are expected to be useful when used with alkylating agents, angiogenesis inhibitors, antibodies, antimetabolites, antimitotics, antiproliferatives, aurora kinase inhibitors, Bcl-2 family protein (for example, Bcl-xL, Bcl-2, Bcl-w, Bfl-1) inhibitors, Bcr-Abl kinase inhibitors, biologic response modifiers, cyclin-dependent kinase inhibitors, cell cycle inhibitors, cyclooxygenase-2 inhibitors, leukemia viral oncogene homolog (ErbB2) receptor inhibitors, growth factor inhibitors, heat shock protein HSP-90 inhibitors, histone deacetylase (HDAC) inhibitors inhibitors, hormonal therapies, immunologicals, intercalating antibiotics, kinase inhibitors, mammalian target of rapomycin inhibitors, mitogen-activated extracellular signal-regulated kinase inhibitors, non-steroidal anti-inflammatory drugs (NSAID's), platinum chemotherapeutics, polo-like kinase inhibitors, proteasome inhibitors, purine analogs, pyrimidine analogs, receptor tyrosine kinase inhibitors, retinoids/deltoids plant alkaloids, topoisomerase inhibitors and the like.

Alkylating agents include altretamine, AMD-473, AP-5280, apaziquone, bendamustine, brostallicin, busulfan, carboquone, carmustine (BCNU), chlorambucil, Cloretazine™ (VNP 40101M), cyclophosphamide, decarbazine, estramustine, fotemustine, glufosfamide, ifosfamide, KW-2170, lomustine (CCNU), mafosfamide, melphalan, mitobronitol, mitolactol, nimustine, nitrogen mustard N-oxide, ranimustine, temozolomide, thiotepa, treosulfan, trofosfamide and the like.

Angiogenesis inhibitors include endothelial-specific receptor tyrosine kinase (Tie-2) inhibitors, epidermal growth factor receptor (EGFR) inhibitors, insulin growth factor-2 receptor (IGFR-2) inhibitors, matrix metalloproteinase-2 (MMP-2) inhibitors, matrix metalloproteinase-9 (MMP-9) inhibitors, platelet-derived growth factor receptor (PDGFR) inhibitors, thrombospondin analogs vascular endothelial growth factor receptor tyrosine kinase (VEGFR) inhibitors and the like.

Aurora kinase inhibitors include AZD-1152, MLN-8054, VX-680 and the like.

Bcl protein family member inhibitors include AT-101 ((−)gossypol), GENASENSE® (G3139 or oblimersen (Bcl-2-targeting antisense oglionucleotide)), IPI-194, IPI-565, N-(4-(4-((4'-chloro(1,1'-biphenyl)-2-yl)methyl)piperazin-1-yl) benzoyl)-4-(((1R)-3-(dimethylamino)-1-((phenylsulfanyl) methyl)propyl)amino)-3-nitrobenzenesulfonamide) (ABT-737), N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl) propyl)amino)-3-((trifluoromethyl)sulfonyl) benzenesulfonamide (ABT-263), GX-070 (obatoclax) and the like.

Bcr-Abl kinase inhibitors include DASATINIB® (BMS-354825), GLEEVEC® (imatinib) and the like.

CDK inhibitors include AZD-5438, BMI-1040, BMS-032, BMS-387, CVT-2584, flavopyridol, GPC-286199, MCS-5A, PD0332991, PHA-690509, seliciclib (CYC-202, R-roscovitine), ZK-304709 and the like.

COX-2 inhibitors include ABT-963, ARCOXIA® (etoricoxib), BEXTRA® (valdecoxib), BMS347070, CELEBREX™ (celecoxib), COX-189 (lumiracoxib), CT-3, DERAMAXX® (deracoxib), JTE-522, 4-methyl-2-(3,4-dimethylphenyl)-1-(4-sulfamoylphenyl-1H-pyrrole), MK-663 (etoricoxib), NS-398, parecoxib, RS-57067, SC-58125, SD-8381, SVT-2016, S-2474, T-614, VIOXX® (rofecoxib) and the like.

EGFR inhibitors include ABX-EGF, anti-EGFr immunoliposomes, EGF-vaccine, EMD-7200, ERBITUX® (cetuximab), HR3, IgA antibodies, IRESSA® (gefitinib), TARCEVA® (erlotinib or OSI-774), TP-38, EGFR fusion protein, TYKERB (lapatinib) and the like.

ErbB2 receptor inhibitors include CP-724-714, CI-1033 (canertinib), Herceptin® (trastuzumab), TYKERB (lapatinib), OMNITARG® (2C4, petuzumab), TAK-165, GW-572016 (ionafarnib), GW-282974, EKB-569, PI-166, dHER2 (HER2 vaccine), APC-8024 (HER-2 vaccine), anti-HER/2neu bispecific antibody, B7.her2IgG3, AS HER2 trifunctional bispecific antibodies, mAB AR-209, mAB 2B-1 and the like.

Histone deacetylase inhibitors include depsipeptide, LAQ-824, MS-275, trapoxin, suberoylanilide hydroxamic acid (SAHA), TSA, valproic acid and the like.

HSP-90 inhibitors include 17-AAG-nab, 17-AAG, CNF-101, CNF-1010, CNF-2024, 17-DMAG, geldanamycin, IPI-504, KOS-953, MYCOGRAB®, NCS-683664, PU24FCl, PU-3, radicicol, SNX-2112, STA-9090 VER49009 and the like.

MEK inhibitors include ARRY-142886, ARRY-438162 PD-325901, PD-98059 and the like.

mTOR inhibitors include AP-23573, CCl-779, everolimus, RAD-001, rapamycin, temsirolimus and the like.

Non-steroidal anti-inflammatory drugs include AMIGESIC® (salsalate), DOLOBID® (diflunisal), MOTRIN (ibuprofen), ORUDIS® (ketoprofen), RELAFEN® (nabumetone), FELDENE® (piroxicam) ibuprofin cream, ALEVE® and NAPROSYN® (naproxen), VOLTAREN® (diclofenac), INDOCIN® (indomethacin), CLINORIL® (sulindac), TOLECTIN® (tolmetin), LODINE® (etodolac), TORADOL® (ketorolac), DAYPRO® (oxaprozin) and the like.

PDGF inhibitors include C-451, CP-673, CP-868596 and the like.

Platinum chemotherapeutics include cisplatin, ELOXATIN® (oxaliplatin) eptaplatin, lobaplatin, nedaplatin, PARAPLATIN® (carboplatin), satraplatin and the like.

Polo-like kinase inhibitors include BI-2536 and the like.

Thrombospondin analogs include ABT-510, ABT-567, ABT-898, TSP-1 and the like.

VEGFR inhibitors include AVASTIN® (bevacizumab), ABT-869, AEE-788, ANGIOZYME™, axitinib (AG-13736), AZD-2171, CP-547,632, IM-862, Macugen (pegaptamib), NEXAVAR® (sorafenib, BAY43-9006), pazopanib (GW-786034), (PTK-787, ZK-222584), SUTENT® (sunitinib, SU-11248), VEGF trap, vatalanib, ZACTIMA™ (vandetanib, ZD-6474) and the like.

Antimetabolites include ALIMTA® (premetrexed disodium, LY231514, MTA), 5-azacitidine, XELODA® (capecitabine), carmofur, LEUSTAT® (cladribine), clofarabine, cytarabine, cytarabine ocfosfate, cytosine arabinoside, decitabine, deferoxamine, doxifluridine, eflornithine, EICAR, enocitabine, ethnylcytidine, fludarabine, hydroxyurea, 5-fluorouracil (5-FU) alone or in combination with leucovorin, GEMZAR® (gemcitabine), hydroxyurea, ALKERAN® (melphalan), mercaptopurine, 6-mercaptopurine riboside, methotrexate, mycophenolic acid, nelarabine, nolatrexed, ocfosate, pelitrexol, pentostatin, raltitrexed, Ribavirin, triapine, trimetrexate, S-1, tiazofurin, tegafur, TS-1, vidarabine, UFT and the like.

Antibiotics include intercalating antibiotics aclarubicin, actinomycin D, amrubicin, annamycin, adriamycin, BLENOXANE® (bleomycin), daunorubicin, CAELYX® or MYOCET® (doxorubicin), elsamitrucin, epirbucin, glarbuicin, ZAVEDOS® (idarubicin), mitomycin C, nemorubicin, neocarzinostatin, peplomycin, pirarubicin, rebeccamycin, stimalamer, streptozocin, VALSTAR® (valrubicin), zinostatin and the like.

Topoisomerase inhibitors include aclarubicin, 9-aminocamptothecin, amonafide, amsacrine, becatecarin, belotecan, BN-80915, CAMPTOSAR® (irinotecan hydrochloride), camptothecin, CARDIOXANE® (dexrazoxine), diflomotecan, edotecarin, ELLENCEk® or PHARMORUBICIN® (epirubicin), etoposide, exatecan, 10-hydroxycamptothecin, gimatecan, lurtotecan, mitoxantrone, orathecin, pirarbucin, pixantrone, rubitecan, sobuzoxane, SN-38, tafluposide, topotecan and the like.

Antibodies include AVASTIN® (bevacizumab), CD40-specific antibodies, chTNT-1/B, denosumab, ERBITUX® (cetuximab), HUMAX-CD4® (zanolimumab), IGF1R-specific antibodies, lintuzumab, PANOREX® (edrecolomab), RENCAREX® (WX G250), RITUXAN® (rituximab), ticilimumab, trastuzimab and the like.

Hormonal therapies include ARIMIDEX® (anastrozole), AROMASIN® (exemestane), arzoxifene, CASODEX® (bicalutamide), CETROTIDE® (cetrorelix), degarelix, deslorelin, DESOPAN® (trilostane), dexamethasone, DROGENIL®, (flutamide), EVISTA® (raloxifene), fadrozole, FARESTON® (toremifene), FASLODEX® (fulvestrant), FMARA®, (letrozole), formestane, glucocorticoids, HECTOROL® or RENAGEL® (doxercalciferol), lasofoxifene, leuprolide acetate, MEGACE® (megesterol), MIFEPREX® (mifepristone), NILANDRON™ (nilutamide), NOLVADEX® (tamoxifen citrate), PLENAXIS™ (abarelix), predisone, PROPECIA® (finasteride), rilostane, SUPREFACT® (buserelin), TRELSTAR® (luteinizing hormone releasing hormone (LHRH)), vantas, VETORYL®, (trilostane or modrastane), ZOLADEX® (fosrelin, goserelin) and the like.

Deltoids and retinoids include seocalcitol (EB1089, CB1093), lexacalcitrol (KH1060), fenretinide, PANRETIN® (aliretinoin), ATRAGEN® (liposomal tretinoin), TARGRETIN® (bexarotene), LGD-1550 and the like.

Plant alkaloids include, but are not limited to, vincristine, vinblastine, vindesine, vinorelbine and the like.

Proteasome inhibitors include VELCADE® (bortezomib), MG132, NPI-0052, PR-171 and the like.

Examples of immunologicals include interferons and other immune-enhancing agents. Interferons include interferon alpha, interferon alpha-2a, interferon alpha-2b, interferon beta, interferon gamma-1a, ACTIMMUNE® (interferon gamma-1b), or interferon gamma-n1, combinations thereof and the like. Other agents include ALFAFERONE®, BAM-002, BEROMUN® (tasonermin), BEXXAR® (tositumomab), CamPath® (alemtuzumab), CTLA4 (cytotoxic lymphocyte antigen 4), decarbazine, denileukin, epratuzumab, GRANOCYTE® (lenograstim), lentinan, leukocyte alpha interferon, imiquimod, MDX-010, melanoma vaccine, mitumomab, molgramostim, MYLOTARG™ (gemtuzumab ozogamicin), NEUPOGEN® (filgrastim), OncoVAC-CL, OvaRex® (oregovomab), pemtumomab (Y-muHMFG1), PROVENGE®, sargaramostim, sizofilan, teceleukin, TheraCys®, ubenimex, VIRULIZIN®, Z-100, WF-10, PROLEUKIN® (aldesleukin), ZADAXIN® (thymalfasin), ZENAPAX® (daclizumab), ZEVALIN® (90Y-Ibritumomab tiuxetan) and the like.

Biological response modifiers are agents that modify defense mechanisms of living organisms or biological responses, such as survival, growth, or differentiation of tissue cells to direct them to have anti-tumor activity and include include krestin, lentinan, sizofuran, picibanil PF-3512676 (CpG-8954), ubenimex and the like.

Pyrimidine analogs include cytarabine (ara C or Arabinoside C), cytosine arabinoside, doxifluridine, FLUDARA® (fludarabine), 5-FU (5-fluorouracil), floxuridine, GEMZAR® (gemcitabine), TOMUDEX® (ratitrexed), TROXATYL™ (triacetyluridine troxacitabine) and the like.

Purine analogs include LANVIS® (thioguanine) and PURI-NETHOL® (mercaptopurine).

Antimitotic agents include batabulin, epothilone D (KOS-862), N-(2-((4-hydroxyphenyl)amino)pyridin-3-yl)-4-methoxybenzenesulfonamide, ixabepilone (BMS 247550), paclitaxel, TAXOTERE (docetaxel), PNU100940 (109881), patupilone, XRP-9881, vinflunine, ZK-EPO and the like.

Compounds of the present invention are also intended to be used as a radiosensitizer that enhances the efficacy of radiotherapy. Examples of radiotherapy include, but are not limited to, external beam radiotherapy, teletherapy, brachtherapy and sealed and unsealed source radiotherapy.

Additionally, compounds having Formula I may be combined with other chemotherapeutic agents such as ABRAXANE™ (ABI-007), ABT-100 (farnesyl transferase inhibitor), ADVEXIN®, ALTOCOR® or MEVACOR® (lovastatin), AMPLIGEN® (poly I:poly C12U, a synthetic RNA), APTOSYN™ (exisulind), AREDIA® (pamidronic acid), arglabin, L-asparaginase, atamestane (1-methyl-3,17-dione-androsta-1,4-diene), AVAGE® (tazarotne), AVE-8062, BEC2 (mitumomab), cachectin or cachexin (tumor necrosis factor), canvaxin (vaccine), CeaVac™ (cancer vaccine), CELEUK® (celmoleukin), CEPLENE® (histamine dihydrochloride), CERVARIX™ (human papillomavirus vaccine), CHOP® (C: CYTOXAN® (cyclophosphamide); H: ADRIAMYCIN® (hydroxydoxorubicin); O: Vincristine (ONCOVIN®); P: prednisone), CyPat™, combrestatin A4P, DAB(389)EGF or TransMID-107R™ (diphtheria toxins), dacarbazine, dactinomycin, 5,6-dimethylxanthenone-4-acetic acid (DMXAA), eniluracil, EVIZON™ (squalamine lactate), DIMERICINE® (T4N5 liposome lotion), discodermolide, DX-8951f (exatecan mesylate), enzastaurin, EP0906, GARDASIL® (quadrivalent human papillomavirus (Types 6, 11, 16, 18) recombinant vaccine), gastrimmune, genasense, GMK (ganglioside conjugate vaccine), GVAX® (prostate cancer vaccine), halofuginone, histerelin, hydroxycarbamide, ibandronic acid, IGN-101, IL-13-PE38, IL-13-PE38QQR (cintredekin besudotox), IL-13-pseudomonas exotoxin, interferon-α, interferon-γ, JUNOVAN™ or MEPACT™ (mifamurtide), lonafarnib, 5,10-methylenetetrahydrofolate, miltefosine (hexadecylphosphocholine), NEOVASTAT® (AE-941), NEUTREXIN® (trimetrexate glucuronate), NIPENT® (pentostatin), ONCONASE® (a ribonuclease enzyme), ONCOPHAGE® (melanoma vaccine treatment), OncoVAX (IL-2 Vaccine), ORATHECIN™ (rubitecan), OSIDEM® (antibody-based cell drug), OvaRex® MAb (murine monoclonal antibody), paditaxel, PANDIMEX™ (aglycone saponins from ginseng comprising 20(S)protopanaxatriol (aPPD) and 20(S)protopanaxatriol (aPPT)), panitumumab, PANVAC®-VF (investigational cancer vaccine), pegaspargase, PEG Interferon A, phenoxodiol, procarbazine, rebimastat, REMOVAB® (catumaxomab), REVLIMID® (lenalidomide), RSR13 (efaproxiral), SOMATULINE® LA (lanreotide), SORIATANE® (acitretin), staurosporine (Streptomyces staurospores), talabostat (PT100), TARGRETIN® (bexarotene), Taxoprexin® (DHA-paclitaxel), TELCYTA™ (TLK286), temilifene, TEMODAR® (temozolomide), tesmilifene, thalidomide, THERATOPE® (STn-KLH), thymitaq (2-amino-3,4-dihydro-6-methyl-4-oxo-5-(4-pyridylthio)quinazoline dihydrochloride), TNFerade™ (adenovector: DNA carrier containing the gene for tumor necrosis factor-α), TRACLEER® or ZAVESCA® (bosentan), tretinoin (Retin-A), tetrandrine, TRISENOX® (arsenic trioxide), VIRULIZIN®, ukrain (derivative of alkaloids from the greater celandine plant), vitaxin (anti-alphavbeta3 antibody), XCYTRIN® (motexafin gadolinium), XINLAY™ (atrasentan), XYOTAX™ (paclitaxel poliglumex), YONDELIS™ (trabectedin), ZD-6126, ZINECARD (dexrazoxane), zometa (zolendronic acid), zorubicin and the like.

It is also expected that compounds having Formula I would inhibit growth of cells derived from a pediatric cancer or neoplasm including embryonal rhabdomyosarcoma, pediatric acute lymphoblastic leukemia, pediatric acute myelogenous leukemia, pediatric alveolar rhabdomyosarcoma, pediatric anaplastic ependymoma, pediatric anaplastic large cell lymphoma, pediatric anaplastic medulloblastoma, pediatric atypical teratoid/rhabdoid tumor of the central nervous syatem, pediatric biphenotypic acute leukemia, pediatric Burkitts lymphoma, pediatric cancers of Ewing's family of tumors such as primitive neuroectodermal rumors, pediatric diffuse anaplastic Wilm's tumor, pediatric favorable histology Wilm's tumor, pediatric glioblastoma, pediatric medulloblastoma, pediatric neuroblastoma, pediatric neuroblastoma-derived myelocytomatosis, pediatric pre-B-cell cancers (such as leukemia), pediatric psteosarcoma, pediatric rhabdoid kidney tumor, pediatric rhabdomyosarcoma, and pediatric T-cell cancers such as lymphoma and skin cancer and the like (commonly-owned U.S. application Ser. No. 10/988,338), Cancer Res., 2000, 60, 6101-10); and autoimmune disorders include, acquired immunodeficiency disease syndrome, autoimmune lymphoproliferative syndrome, hemolytic anemia, inflammatory diseases, thrombocytopenia and the like (Current Allergy and Asthma Reports 2003, 3:378-384; Br. J. Haematol. 2000 September; 110(3): 584-90; Blood 2000 Feb. 15; 95(4):1283-92; and New England Journal of Medicine 2004 September; 351(14): 1409-1418).

For example, involvement of Aurora-kinases in bladder cancer, breast cancer, cervical cancer, colon cancer, endometrial cancer, esophageal cancer, lung cancer, ovarian cancer, pancreatic cancer, prostate cancer, rectal cancer, skin cancer, stomach cancer and thyroid cancer is reported in Nature Reviews/Cancer, Vol. 4 December, 2004.

Compounds having Formula I may be made by synthetic chemical processes, examples of which are shown hereinbelow. It is meant to be understood that the order of the steps in the processes may be varied, that reagents, solvents and reaction conditions may be substituted for those specifically mentioned, and that vulnerable moieties may be protected and deprotected, as necessary.

Protecting groups for C(O)OH moieties include, but are not limited to, acetoxymethyl, allyl, benzoylmethyl, benzyl, benzyloxymethyl, tert-butyl, tert-butyldiphenylsilyl, diphenylmethyl, cyclobutyl, cyclohexyl, cyclopentyl, cyclopropyl, diphenylmethylsilyl, ethyl, para-methoxybenzyl, methoxymethyl, methoxyethoxymethyl, methyl, methylthiomethyl, naphthyl, para-nitrobenzyl, phenyl, n-propyl, 2,2,2-trichloroethyl, triethylsilyl, 2-(trimethylsilyl)ethyl, 2-(trimethylsilyl)ethoxymethyl, triphenylmethyl and the like.

Protecting groups for C(O) and C(O)H moieties include, but are not limited to, 1,3-dioxylketal, diethylketal, dimethylketal, 1,3-dithianylketal, O-methyloxime, O-phenyloxime and the like.

Protecting groups for NH moieties include, but are not limited to, acetyl, alanyl, benzoyl, benzyl (phenylmethyl), benzylidene, benzyloxycarbonyl (Cbz), tert-butoxycarbonyl (Boc), 3,4-dimethoxybenzyloxycarbonyl, diphenylmethyl, diphenylphosphoryl, formyl, methanesulfonyl, para-methoxybenzyloxycarbonyl, phenylacetyl, phthaloyl, succinyl, trichloroethoxycarbonyl, triethylsilyl, trifluoroacetyl, trimethylsilyl, triphenylmethyl, triphenylsilyl, para-toluenesulfonyl and the like.

Protecting groups for OH and SH moieties include, but are not limited to, acetyl, allyl, allyloxycarbonyl, benzyloxycarbonyl (Cbz), benzoyl, benzyl, tert-butyl, tert-butyldimethylsilyl, tert-butyldiphenylsilyl, 3,4-dimethoxybenzyl, 3,4-dimethoxybenzyloxycarbonyl, 1,1-dimethyl-2-propenyl, diphenylmethyl, formyl, methanesulfonyl, methoxyacetyl, 4-methoxybenzyloxycarbonyl, para-methoxybenzyl, methoxycarbonyl, methyl, para-toluenesulfonyl, 2,2,2-trichloroethoxycarbonyl, 2,2,2-trichloroethyl, triethylsilyl, trifluoroacetyl, 2-(trimethylsilyl)ethoxycarbonyl, 2-trimethylsilylethyl, triphenylmethyl, 2-(triphenylphosphonio)ethoxycarbonyl and the like.

The following abbreviations have the meanings indicated. ADDP means 1,1'-(azodicarbonyl)dipiperidine; AD-mix-β means a mixture of (DHQD)$_2$PHAL, K$_3$Fe(CN)$_6$, K$_2$CO$_3$ and K$_2$SO$_4$); AIBN means 2,2'-azobis(2-methylpropionitrile); 9-BBN means 9-borabicyclo(3.3.1)nonane; Cp means cyclopentadiene; (DHQD)$_2$PHAL means hydroquinidine 1,4-phthalazinediyl diethyl ether; DBU means 1,8-diazabicyclo (5.4.0)undec-7-ene; DCC means 1,3-dicyclohexylcarbodiimide, DIBAL means diisobutylaluminum hydride; DIEA means diisopropylethylamine; DMAP means N,N-dimethylaminopyridine; DME means 1,2-dimethoxyethane; DMF means N,N-dimethylformamide; dmpe means 1,2-bis(dimethylphosphino)ethane; DMSO means dimethylsulfoxide; dppa means diphenylphosphoryl azide; dppb means 1,4-bis(diphenylphosphino)butane; dppe means 1,2-bis(diphenylphosphino)ethane; dppf means 1,1'-bis(diphenylphosphino)ferrocene; dppm means 1,1-bis(diphenylphosphino)methane; EDAC or EDCI or EDC means 1-(3-dimethylaminopropyl)-3-ethylcarbodiimide; Fmoc means fluorenylmethoxycarbonyl; HATU means O-(7-azabenzotriazol-1-yl)-N,N,N',N'-tetramethyluronium hexafluorophosphate; HMPA means hexamethylphosphoramide; HOAT means 1-hydroxy-7-azabenzotriazole; HOBT means 1-hydroxybenzotriazole hydrate, IPA means isopropyl alcohol; LDA means lithium diisopropylamide; LHMDS means lithium bis(hexamethyldisilylamide); MP-BH$_3$ means macroporus triethylammonium methylpolystyrene cyanoborohydride; LAH means lithium aluminum hydride; NCS means N-chlorosuccinimide; PyBOP means benzotriazol-1-yloxytripyrrolidinophosphonium hexafluorophosphate; TBTU means O-benzotriazol-1-yl-N,N,N',N'-tetramethyluronium tetrafluoroborate; TDA-1 means tris(2-(2-methoxyethoxy)ethyl)amine; TEA means triethylamine; TFA means trifluoroacetic acid; THF means tetrahydrofuran; NCS means N-chlorosuccinimide; NMM means N-methylmorpholine; NMP means N-methylpyrrolidine; PPh$_3$ means triphenylphosphine.

The following scheme and examples are presented to provide what is believed to be the most useful and readily understood description of procedures and conceptual aspects of this invention.

Compounds having Formula (1) can be prepared a number of ways, such as ones described in Can. J. Chem. 2001, 79, 1827-1839.

SCHEME 1

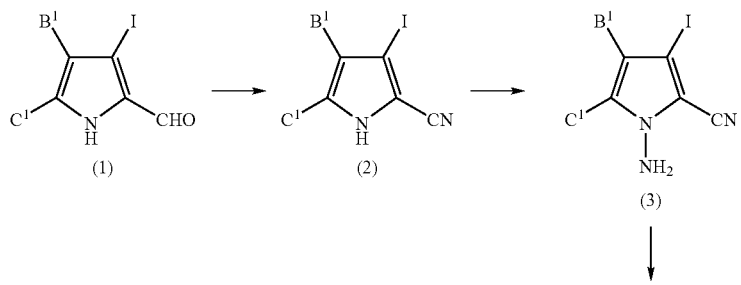

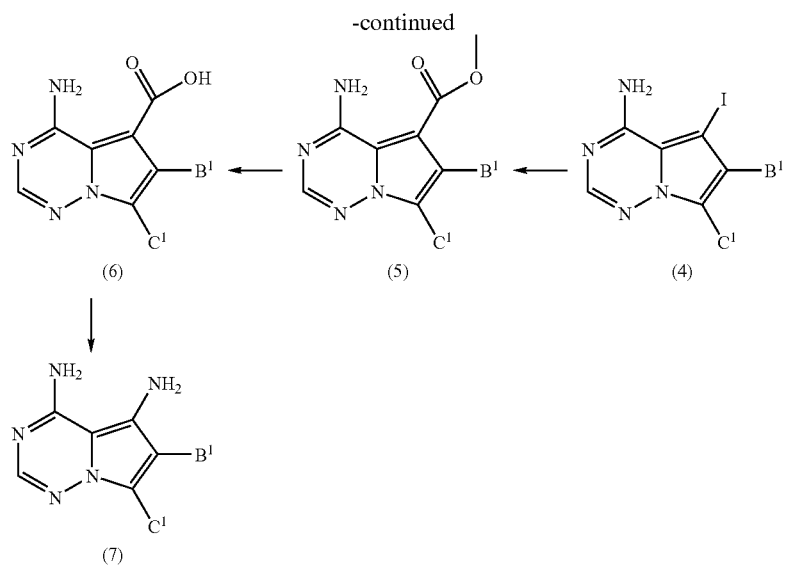

As shown in SCHEME 1, compounds having Formula (1) can be converted to compounds having Formula (2) by reacting the former and hydroxylamine hydrochloride and reacting the product therefrom and acetic anhydride. The first reaction is typically conducted between about 20° C. to 40° C., over about 8 to about 20 hours, in solvents such as pyridine and the like. The second reaction is typically conducted between about 70° C. to 90° C., over about 4 to about 8 hours.

Compounds having Formula (2) can be converted to compounds having Formula (3) by reacting the former and sodium hydride and reacting the product therefrom and O-(diphenylphosphoryl)hydroxylamine.

The first reaction is typically conducted between about 20° C. to 40° C., over about 1 to about 30 minutes, in solvents such as DMF, dichloromethane, THF or, mixtures thereof and the like. The second reaction is typically conducted between about 20° C. to 40° C., over about 30 minutes to about 4 hours, in solvents such as DMF, dichloromethane, THF, mixtures thereof and the like.

Compounds having Formula (3) can be converted to compounds having Formula (4) by reacting the former, triethylorthoformate and sulfamide and reacting the product thereform and ammonia. The first reaction is typically conducted at reflux, over about one to about two hours, using triethylorthoformate as the solvent.

The second reaction is typically conducted between about 20° C. to 40° C., over about 8 to about 20 hours, in solvents such as the ammonia or in methanol, ethanol, mixtures thereof and the like.

Compounds having Formula (4) can be converted to compounds having Formula (5) by reacting the former, carbon monoxide, methanol, a palladium catalyst, and a second base. Examples of palladium catalysts include palladium acetate, (1,1'-bis(diphenylphosphino)ferrocene)dichloropalladium (II), and the like. Examples of second bases include TEA, pyridine and the like. The reaction is typically conducted (in a sealed container), over about one to about three hours, between about 80° C. and 120° C., in the methanol.

Compounds having Formula (5) can be converted to compounds having Formula (6) by reacting the former and a first base. Examples of first bases include lithium hydroxide, sodium hydroxide, potassium hydroxide and the like. The reaction is typically conducted over about 1 hour to about 48 hours, between about 0° C. and 35° C., in solvents such as water, methanol, ethanol, isopropanol, mixtures thereof and the like.

Introduction of moieties represented by $A^1$ can be accomplished by reacting compounds having formula (6), a primary or a secondary amine, a coupling agent, a second base, with or without a coupling auxiliary. Examples of coupling agents include DCC, EDCI, HATU, TBTU and the like. Examples of second bases include DIEA, TEA, NMM and the like. Examples of coupling auxiliaries include DMAP, HOAT, HOBT and the like. The reaction is typically conducted between about 25° C. to 45° C., over about 1 to about 24 hours, in solvents such as THF, DMF, dichloromethane, ethyl acetate, mixtures thereof and the like.

Compounds having Formula (6) can be converted to compounds having Formula (7) by reacting the former and DPPA followed by hydrolysis of the isocyanate intermediate with water. The reactions are typically conducted over about 1 hour to about 24 hours, between about 50° C. and 110° C., in solvents such as benzene, toluene, THF, water, mixtures thereof and the like.

Introduction of moieties represented by $A^1$ can also be accomplished by reacting the compounds having Formula (7) and the appropriate isocyanate, carbonyl chloride, sulfonyl chloride, or carbamoyl chloride. The reactions are typically conducted over about 1 hour to about 48 hours, between about 0° C. and 110° C., in solvents such as THF, ethyl acetate, dichloromethane, DMF, DMSO, chloroform, mixtures thereof and the like.

EXAMPLE 1A

A mixture of (3-chloropyrazin-2-yl)methanamine (4.9 g), acetic acid (2.25 g), EDC (7.2 g), HOBT (5.75 g) and NMM (6.9 g) in dichloromethane (40 mL) was stirred at room temperature for 48 hours, treated with water and extracted with ethyl acetate. The extract was washed with brine, dried (MgSO$_4$), filtered and concentrated. The concentrate was purified by flash chromatography on silica gel with 0-5% methanol/dichloromethane.

EXAMPLE 1B

A mixture of EXAMPLE 1A (3.98 g) and acetonitrile (100 mL) was treated with DMF (100 µL) and POCl$_3$ (9.8 mL). The mixture was heated at 55° C. for 30 minutes cooled to room temperature and concentrated. The concentrate was dissolved in dichloromethane, neutralized with pre-cooled ammonia in isopropanol and concentrated. The concentrate was partitioned between dichloromethane and water, and the extract was washed with brine and dried ($MgSO_4$), filtered and concentrated. The concentrate was dissolved in dichloromethane and purified by flash chromatography on silica gel with 0-5% methanol/dichloromethane.

EXAMPLE 1C

A mixture of EXAMPLE 1B (2.83 g) and NIS (4.94 g) in DMF (20 mL) was heated at 60° C. for 3 hours, cooled to room temperature, diluted with water and extracted with ethyl acetate. The extract was washed with brine, dried ($MgSO_4$), filtered and concentrated; and the concentrate was triturated with hexanes and filtered.

EXAMPLE 1D

In a stainless steel reactor, EXAMPLE 1C (3.3 g) in 2M $NH_3$ in isopropanol (45 mL) and THF (4 mL) was cooled with a dry ice-acetone bath and treated with anhydrous $NH_3$ (15 mL). The mixture was heated at 110° C. for 48 hours, cooled to room temperature and vented. The mixture was concentrated, and the concentrate was triturated with water and filtered. The filtrate was extracted with ethyl acetate and the extract was washed with brine, dried ($MgSO_4$), filtered and concentrated. The concentrate was purified by flash chromatography on silica gel with 0-5% methanol/dichloromethane.

EXAMPLE 1E

A mixture of EXAMPLE 1D (1.3 g), $PdCl_2(dppf)$ (150 mg) and triethylamine (0.480 g) in methanol (10 mL) was purged with CO, sealed and heated at 100° C. for 2 hours under 60 psi. The reaction mixture was concentrated and the concentrate was purified by flash chromatography on silica gel with 0-5% methanol/dichloromethane.

EXAMPLE 1F

A mixture of EXAMPLE 1E (0.87 g) and 2N LiOH (10 mL) in methanol (10 mL) was stirred at room temperature for 3 hours, neutralized with 2N HCl to pH 6-7, and filtered.

EXAMPLE 1G 1-fluoro-3-isocyanatobenzene (0.56 mL) was added to a solution of (4-aminophenyl)carbamic acid tert-butyl ester (1.04 g) in dichloromethane (20 mL) at 0° C. The mixture was stirred at ambient temperature for 4 hours and filtered. The filtrant was collected was suspended in dichloromethane (20 mL), cooled in an ice bath, treated with TFA (5 mL), stirred for 15 minutes at ambient temperature for 3 hours and concentrated. The concentrate was concentrated twice from methanol and toluene and dried to provide the title compound as the trifluoroacetate salt.

EXAMPLE 1H

A mixture of TEA (61 mg), EXAMPLE 1F (0.038 g), EXAMPLE 1G trifluoroacatate (0.072 g) and HATU (0.084 g) in DMF (2 mL) was stirred at ambient temperature for 20 hours and extracted with ethyl acetate. The extract was washed with brine, dried ($MgSO_4$), filtered and concentrated. The concentrate was purified by flash chromatography on silica gel with 0 to 5% methanol/dichloromethane. $^1H$ NMR (500 MHz, DMSO-$d_6$) δ 2.62 (s, 3H), 6.55-6.90 (m, 1H), 6.98-7.64 (m, 8H), 7.75 (d, J=8.85 Hz, 2H), 8.71 (s, 1H), 8.88 (s, 1H), 9.26 (s, 1H), 10.22 (s, 1H).

EXAMPLE 2

This example was prepared by substituting 1-(4-aminophenyl)-3-phenylurea for EXAMPLE 1G in EXAMPLE 1H. $^1H$ NMR (400 MHz, DMSO-$d_6$) δ 2.62 (s, 3H), 6.96 (t, J=7.36 Hz, 1H), 7.18 (d, J=4.91 Hz, 1H), 7.28 (t, J=7.83 Hz, 2H), 7.38-7.58 (m, 5H), 7.74 (d, J=8.90 Hz, 2H), 8.62 (s, 2H), 10.18 (s, 1H).

EXAMPLE 3

This example was prepared by substituting N-(4-aminophenyl)benzamide for EXAMPLE 1G in EXAMPLE 1H $^1H$ NMR (300 MHz, DMSO-$d_6$) δ 2.63 (s, 3H), 7.19 (d, J=4.76 Hz, 1H), 7.46-7.64 (m, 4H), 7.71-7.86 (m, 4H), 7.91-8.01 (m, 2H), 10.24 (s, 1H), 10.28 (s, 1H).

EXAMPLE 4

This example was prepared as described in EXAMPLES 1G-1H by substituting 1-isocyanato-3-(trifluoromethyl)benzene for 1-fluoro-3-isocyanatobenzene in EXAMPLE 1G. $^1H$ NMR (300 MHz, DMSO-$d_6$) δ 2.62 (s, 3H), 7.18 (d, J=4.76 Hz, 1H), 7.30 (d, J=7.14 Hz, 1H), 7.39-7.64 (m, 5H), 7.76 (d, J=8.73 Hz, 2H), 8.02 (s, 1H), 8.76 (s, 1H), 9.02 (s, 1H), 10.22 (s, 1H).

EXAMPLE 5

This example was prepared as described in EXAMPLE 1G-H by substituting tert-butyl 3-(aminomethyl)phenylcarbamate for (4-aminophenyl)carbamic acid tert-butyl ester in EXAMPLE 1G. $^1H$ NMR (300 MHz, DMSO-$d_6$) δ 2.62 (s, 3H), 4.31 (d, J=5.95 Hz, 2H), 6.58-6.81 (m, 2H), 7.05 (d, J=7.93 Hz, 2H), 7.15-7.35 (m, 3H), 7.39-7.57 (m, 2H), 7.68 (d, J=9.12 Hz, 1H), 7.83 (s, 1H), 8.82 (s, 1H), 10.27 (s, 1H).

EXAMPLE 6

This example was prepared as described in EXAMPLE 1G-H by substituting tert-butyl 3-(aminomethyl)phenylcarbamate and isocyanatobenzene for (4-aminophenyl)carbamic acid tert-butyl ester and 1-fluoro-3-isocyanatobenzene, respectively in EXAMPLE 1G. $^1H$ NMR (300 MHz, DMSO-$d_6$) δ 2.61 (s, 3H), 4.30 (d, J=5.76 Hz, 2H), 6.61 (t, J=5.76 Hz, 1H), 6.89 (t, J=7.29 Hz, 1H), 7.06 (d, J=8.14 Hz, 1H), 7.15-7.46 (m, 6H), 7.67 (d, J=8.14 Hz, 1H), 7.67 (d, J=8.14 Hz, 1H), 7.84 (s, 1H), 8.55 (s, 1H), 10.26 (s, 1H).

EXAMPLE 7

This example was prepared as described in EXAMPLE 1G-H by substituting tert-butyl 3-(aminomethyl)phenylcarbamate and 1-fluoro-2-isocyanatobenzene for (4-aminophenyl)carbamic acid tert-butyl ester and 1-fluoro-3-isocyanatobenzene, respectively in EXAMPLE 1G$^1$. $^1H$ NMR (300 MHz, DMSO-$d_6$) δ 2.62 (s, 3H) 4.33 (d, J=5.76 Hz, 2H) 6.87-6.98 (m, 1H) 7.03-7.24 (m, 5H) 7.32 (t, J=7.80 Hz, 1H) 7.55 (d, J=4.75 Hz, 1H) 7.62-7.74 (m, 1H) 7.84 (s, 1H) 8.00-8.22 (m, 1H) 8.39 (d, J=2.37 Hz, 1H) 10.31 (s, 1H).

EXAMPLE 8

This example was prepared as described in EXAMPLE 1G-H by substituting tert-butyl 3-(aminomethyl)phenylcarbamate and 1-fluoro-4-isocyanatobenzene for (4-aminophenyl)carbamic acid tert-butyl ester and 1-fluoro-3-isocyanatobenzene, respectively, in EXAMPLE 1G. $^1$H NMR (300 MHz, DMSO-$d_6$) δ 2.61 (s, 3H) 4.30 (d, J=5.76 Hz, 2H) 6.61 (t, J=5.76 Hz, 1H) 6.97-7.13 (m, 3H) 7.19 (d, J=4.75 Hz, 1H) 7.30 (t, J=7.80 Hz, 1H) 7.36-7.46 (m, 3H) 7.52 (d, J=4.75 Hz, 1H) 7.67 (d, J=8.14 Hz, 1H) 7.83 (s, 1H) 8.59 (s, 1H).

EXAMPLE 9

This example was prepared as described in EXAMPLE 1G-H by substituting tert-butyl 3-(aminomethyl)phenylcarbamate and 1-isocyanato-4-trifluoromethylbenzene for (4-aminophenyl)carbamic acid tert-butyl ester and 1-fluoro-3-isocyanatobenzene, respectively, in EXAMPLE 1G. $^1$H NMR (300 MHz, DMSO-$d_6$) δ 2.61 (s, 3H) 4.33 (d, J=5.95 Hz, 2H) 6.80 (t, J=5.75 Hz, 1H) 7.07 (d, J=7.54 Hz, 1H) 7.19 (d, J=4.76 Hz, 1H) 7.31 (t, J=7.73 Hz, 1H) 7.45-7.74 (m, 6H) 7.85 (s, 1H) 9.02 (s, 1H) 10.26 (s, 1H).

EXAMPLE 10A

A solution of 2-(3-aminophenyl)ethanol (0.6 g) and 1-isocyanato-4-nitrobenzene (0.82 g) in dichloromethane (20 mL) was stirred at ambient temperature for 1 hourour. The resulting suspension was filtered and the solid collected was dried.

EXAMPLE 10B

A mixture of EXAMPLE 10A (1 g) and 5% Pd/carbon (100 mg) was stirred under hydrogen for 10 hours and filtered. The filtrate was diluted with ethyl acetate and washed with water. A white precipitate that formed in the aqueous layer which was filtered and dried. Additional product was obtained after drying (MgSO$_4$), filtering and concentrating.

EXAMPLE 10C

This example was prepared by substituting EXAMPLE 10B for EXAMPLE 1G in EXAMPLE 1H. $^1$H NMR (300 MHz, DMSO-$d_6$) δ 2.62 (s, 3H), 2.69 (t, J=7.12 Hz, 2H), 3.49-3.68 (m, 2H), 4.63 (t, J=5.26 Hz, 1H), 6.82 (d, J=7.46 Hz, 1H), 7.07-7.22 (m, 2H), 7.24-7.33 (m, 2H), 7.42 (d, J=9.15 Hz, 2H), 7.52 (d, J=5.09 Hz, 1H), 7.73 (d, J=8.81 Hz, 2H), 8.59 (s, 1H), 8.62 (s, 1H), 10.20 (s, 1H).

EXAMPLE 11

This example was prepared as described in EXAMPLE 10 by substituting 2-(4-aminophenyl)ethanol for 2-(3-aminophenyl)ethanol. $^1$H NMR (400 MHz, DMSO-$d_6$) δ 2.62 (s, 3H), 2.66 (t, J=6.90 Hz, 2H), 3.49-3.78 (m, 2H), 4.58 (t, J=4.91 Hz, 1H), 6.89-7.62 (m, 9H) 7.73 (d, J=8.59 Hz, 2H) 8.52 (s, 1H) 8.57 (s, 1H) 9.29 (s, 1H) 10.17 (s, 1H).

EXAMPLE 12A

A mixture of 3-iodo-1H-pyrrole-2-carbaldehyde (2.6 g) and NH2OH.HCl (0.9 g) in pyridine (915 mL) was stirred overnight at ambient temperature, treated with acetic anhydride (1.24 mL) and heated to 90° C. for 6 hours. The reaction mixture was concentrated, the concentrate was partitioned between ethyl acetate and water and the organic extract was washed with brine, dried (MgSO$_4$), filtered and concentrated. The concentrate was purified by flash chromatography on silica gel with 0-20% ethyl acetate/hexanes.

EXAMPLE 12B

A solution of EXAMPLE 12A (0.97 g) in DMF (60 mL) was treated with NaH (214 mg, 60% oil dispersion), stirred at ambient temperature for 5 min, treated with O-(diphenylphosphoryl)hydroxylamine (2.13 g) and stirred an additional 2 hours. The reaction was quenched with pH 7.2 phosphate buffer and extracted with ethyl acetate. The organic extract was washed with brine, dried (MgSO$_4$), filtered and concentrated. The concentrate was purified by flash chromatography on silica gel with ethyl acetate/hexanes.

EXAMPLE 12C

A mixture of EXAMPLE 12B (0.7 g), triethylorthoformate (10 mL) and (NH$_4$)$_2$SO$_4$ (40 mg) was refluxed for 3 hours, cooled to ambient temperature treated with 7N ammonia in methanol (30 mL) and stirred at ambient temperature overnight. The reaction mixture was concentrated, and the concentrate was triturated with water and filtered.

EXAMPLE 12D

This example was prepared as described in EXAMPLES 1E-F by substituting EXAMPLE 12C for EXAMPLE 1D.

EXAMPLE 12E

This example was prepared by substituting EXAMPLE 12D for EXAMPLE 1F in EXAMPLE 1H. $^1$H NMR (300 MHz, DMSO-$d_6$) δ 6.68-6.84 (m, 1H), 7.06-7.16 (m, 1H), 7.22-7.37 (m, 1H), 7.40-7.66 (m, 6H), 7.75 (d, J=3.05 Hz, 1H), 7.93 (s, 1H), 8.16 (s, 1H), 8.72 (s, 1H), 8.87 (s, 1H), 9.97 (s, 1H), 10.08 (s, 1H).

EXAMPLE 13

This example was prepared as described in EXAMPLES 1G-1H by substituting 1-fluoro-4-isocyanatobenzene for 1-fluoro-3-isocyanatobenzene in EXAMPLE 1G and EXAMPLE 12D for 1F in EXAMPLE 1H. $^1$H NMR (300 MHz, DMSO-$d_6$) δ 7.12 (t, J=8.99 Hz, 2H) 7.39-7.52 (m, 4H) 7.53-7.66 (m, 3H) 7.75 (d, J=3.05 Hz, 1H) 7.93 (s, 1H) 8.17 (s, 1H) 8.65 (s, 1H) 8.67 (s, 1H) 9.97 (s, 1H) 10.08 (s, 1H)

EXAMPLE 14

This example was prepared as described in EXAMPLES 1G-1H by substituting 1-fluoro-2-isocyanatobenzene for 1-fluoro-3-isocyanatobenzene in EXAMPLE 1G and EXAMPLE 12D for 1F in EXAMPLE 1H. $^1$H NMR (300 MHz, DMSO-$d_6$) δ 6.93-7.06 (m, 1H) 7.08-7.30 (m, 2H) 7.45 (d, J=9.16 Hz, 2H) 7.53-7.68 (m, 3H) 7.75 (d, J=3.05 Hz, 1H) 7.94 (s, 1H) 8.09-8.26 (m, 2H) 8.52 (d, J=2.37 Hz, 1H) 9.07 (s, 1H) 9.98 (s, 1H) 10.09 (s, 1H).

EXAMPLE 15

This example was prepared as described in EXAMPLES 1G-1H by substituting isocyanatobenzene for 1-fluoro-3-isocyanatobenzene in EXAMPLE 1G and EXAMPLE 12D for 1F in EXAMPLE 1H. $^1$H NMR (300 MHz, DMSO-$d_6$) δ 6.97 (t, J=7.29 Hz, 1H), 7.28 (t, J=7.97 Hz, 2H), 7.39-7.50 (m, 4H), 7.53-7.64 (m, 3H), 7.75 (d, J=3.05 Hz, 1H), 7.93 (s, 1H), 8.17 (s, 1H), 8.65 (d, J=6.10 Hz, 2H), 9.99 (s, 1H), 10.08 (s, 1H).

EXAMPLE 16

This example was prepared as described in EXAMPLES 1G-1H by substituting 1-isocyanato-3,5-dimethylbenzene for 1-fluoro-3-isocyanatobenzene in EXAMPLE 1G and EXAMPLE 12D for 1F in EXAMPLE 1H. $^1$H NMR (300 MHz, DMSO-$d_6$) δ 2.23 (s, 6H) 6.61 (s, 1H) 7.07 (s, 2H) 7.44 (d, J=8.81 Hz, 2H) 7.52-7.66 (m, 3H) 7.75 (d, J=3.05 Hz, 1H) 7.93 (s, 1H) 8.17 (s, 1H) 8.48 (s, 1H) 8.62 (s, 1H) 9.99 (s, 1H) 10.07 (s, 1H).

EXAMPLE 17

This example was prepared as described in EXAMPLES 1G-1H by substituting 1-isocyanato-3-methylbenzene for 1-fluoro-3-isocyanatobenzene in EXAMPLE 1G and EXAMPLE 12D for 1F in EXAMPLE 1H. $^1$H NMR (300 MHz, DMSO-$d_6$) δ 2.28 (s, 3H) 6.79 (d, J=7.12 Hz, 1H) 7.08-7.27 (m, 2H) 7.30 (s, 1H) 7.45 (d, J=8.82 Hz, 2H) 7.52-7.68 (m, 3H) 7.75 (d, J=3.05 Hz, 1H) 7.93 (s, 1H) 8.17 (s, 1H) 8.56 (s, 1H) 8.64 (s, 1H) 9.84-10.05 (m, 1H) 10.08 (s, 1H).

EXAMPLE 18

This example was prepared as described in EXAMPLES 1G-1H by substituting 1-isocyanato-4-methylbenzene for 1-fluoro-3-isocyanatobenzene in EXAMPLE 1G and EXAMPLE 12D for 1F in EXAMPLE 1H. $^1$H NMR (300 MHz, DMSO-$d_6$) δ 2.24 (s, 3H) 7.08 (d, J=8.14 Hz, 2H) 7.34 (d, J=8.48 Hz, 2H) 7.44 (d, J=9.16 Hz, 2H) 7.52-7.64 (m, 3H) 7.74 (d, J=3.05 Hz, 1H) 7.93 (s, 1H) 8.16 (s, 1H) 8.52 (s, 1H) 8.60 (s, 1H) 9.99 (s, 1H) 10.07 (s, 1H)

EXAMPLE 19

This example was prepared as described in EXAMPLES 1G-1H by substituting 1-isocyanato-2-methylbenzene for 1-fluoro-3-isocyanatobenzene in EXAMPLE 1G and EXAMPLE 12D for 1F in EXAMPLE 1H. $^1$H NMR (300 MHz, DMSO-$d_6$) δ 2.25 (s, 3H) 6.86-6.98 (m, 1H) 7.07-7.22 (m, 2H) 7.42-7.52 (m, 2H) 7.54-7.65 (m, 3H) 7.79 (d, J=3.39 Hz, 1H) 7.85 (d, J=7.12 Hz, 1H) 7.93 (s, 1H) 7.97 (s, 1H) 8.33 (s, 1H) 9.07 (s, 1H) 10.12 (s, 1H) 10.17 (s, 1H)

EXAMPLE 20

This example was prepared as described in EXAMPLES 1G-1H by substituting 1-isocyanato-3-methoxybenzene for 1-fluoro-3-isocyanatobenzene in EXAMPLE 1G and EXAMPLE 12D for 1F in EXAMPLE 1H. $^1$H NMR (300 MHz, DMSO-$d_6$) δ 3.74 (s, 3H) 6.55 (dd, J=7.97, 2.20 Hz, 1H) 6.83-7.01 (m, 1H) 7.09-7.27 (m, 2H) 7.35-7.50 (m, 2H) 7.52-7.67 (m, 3H) 7.75 (d, J=3.05 Hz, 1H) 7.93 (s, 1H) 8.17 (s, 1H) 8.65 (d, J=2.03 Hz, 2H) 9.99 (s, 1H) 10.08 (s, 1H)

EXAMPLE 21

This example was prepared as described in EXAMPLES 1G-1H by substituting 1-isocyanato-4-methoxybenzene for 1-fluoro-3-isocyanatobenzene in EXAMPLE 1G and EXAMPLE 12D for 1F in EXAMPLE 1H. $^1$H NMR (300 MHz, DMSO-$d_6$) δ 3.72 (s, 3H) 6.76-6.95 (m, 2H) 7.28-7.49 (m, 4H) 7.52-7.66 (m, 3H) 7.75 (d, J=3.05 Hz, 1H) 7.93 (s, 1H) 8.17 (s, 1H) 8.44 (s, 1H) 8.57 (s, 1H) 9.99 (s, 1H) 10.07 (s, 1H)

EXAMPLE 22

This example was prepared as described in EXAMPLES 1G-1H by substituting 1-isocyanato-3-trifluoromethylbenzene for 1-fluoro-3-isocyanatobenzene in EXAMPLE 1G and EXAMPLE 12D for 1F in EXAMPLE 1H. $^1$H NMR (500 MHz, DMSO-$d_6$) δ 7.31 (d, J=7.63 Hz, 1H) 7.43-7.68 (m, 7H) 7.75 (d, J=2.75 Hz, 1H) 7.94 (s, 1H) 8.04 (s, 1H) 8.19 (s, 1H) 8.82 (s, 1H) 9.06 (s, 1H) 10.00 (s, 1H) 10.11 (s, 1H).

EXAMPLE 23

This example was prepared as described in EXAMPLES 1G-1H by substituting isocyanatocyclopropane for 1-fluoro-3-isocyanatobenzene in EXAMPLE 1G and EXAMPLE 12D for 1F in EXAMPLE 1H. $^1$H NMR (300 MHz, DMSO-$d_6$) δ 0.33-0.45 (m, 2H) 0.56-0.68 (m, 2H) 2.52-2.61 (m, 1H) 6.35 (d, J=2.71 Hz, 1H) 7.39 (d, J=8.82 Hz, 2H) 7.49-7.60 (m, 3H) 7.74 (d, J=3.05 Hz, 1H) 7.93 (s, 1H) 8.17 (d, J=3.39 Hz, 1H) 8.27 (s, 1H) 10.03 (s, 2H).

EXAMPLE 24

This example was prepared as described in EXAMPLES 1G-1H by substituting isocyanatocyclopentane for 1-fluoro-3-isocyanatobenzene in EXAMPLE 1G and EXAMPLE 12D for 1F in EXAMPLE 1H. $^1$H NMR (300 MHz, DMSO-$d_6$) δ 1.21-1.45 (m, 2H) 1.45-1.70 (m, 4H) 1.73-1.97 (m, 2H) 3.71-4.11 (m, 1H) 6.11 (d, J=7.12 Hz, 1H) 7.36 (d, J=8.82 Hz, 2H) 7.44-7.62 (m, 3H) 7.73 (d, J=3.05 Hz, 1H) 7.93 (s, 1H) 8.15 (s, 1H) 8.23 (s, 1H) 10.02 (s, 2H).

EXAMPLE 25

This example was prepared as described in EXAMPLES 1G-1H by substituting 3-isocyanatothiophene for 1-fluoro-3-isocyanatobenzene in EXAMPLE 1G and EXAMPLE 12D for 1F in EXAMPLE 1H. $^1$H NMR (300 MHz, DMSO-$d_6$) δ 7.05 (dd, J=5.09, 1.36 Hz, 1H) 7.21-7.33 (m, 1H) 7.37-7.48 (m, 3H) 7.51-7.66 (m, 3H) 7.75 (d, J=3.05 Hz, 1H) 7.93 (s, 1H) 8.17 (s, 1H) 8.62 (s, 1H) 8.90 (s, 1H) 10.00 (s, 1H) 10.07 (s, 1H).

EXAMPLE 26

This example was prepared as described in EXAMPLES 1G-1H by substituting 2-isocyanatopyridine for 1-fluoro-3-isocyanatobenzene in EXAMPLE 1G and EXAMPLE 12D for 1F in EXAMPLE 1H. $^1$H NMR (300 MHz, DMSO-$d_6$) δ 7.31 (dd, J=8.14, 4.75 Hz, 1H) 7.41-7.52 (m, 2H) 7.54-7.67 (m, 3H) 7.75 (d, J=3.05 Hz, 1H) 7.87-8.00 (m, 2H) 8.19 (dd, J=4.75, 1.36 Hz, 1H) 8.61 (d, J=2.71 Hz, 1H) 8.81 (d, J=5.76 Hz, 2H) 9.98 (s, 1H) 10.09 (s, 1H).

EXAMPLE 27

This example was prepared as described in EXAMPLE 1H by substituting N-(4-aminophenyl)benzamide and 12D, for 1G and 1F respectively. $^1$H NMR (300 MHz, DMSO-$d_6$) δ 7.46-7.64 (m, 4H) 7.64-7.84 (m, 5H) 7.89-8.01 (m, 3H) 8.13-8.19 (m, 1H) 9.97 (s, 1H) 10.14 (s, 1H) 10.26 (s, 1H).

EXAMPLE 28

This example was prepared as described in EXAMPLES 1G-1H by substituting 1-fluoro-2-isocyanato-4-methylbenzene for 1-fluoro-3-isocyanatobenzene in EXAMPLE 1G and EXAMPLE 12D for 1F in EXAMPLE 1H. $^1$H NMR (300 MHz, DMSO-d$_6$) δ 2.28 (s, 3H) 6.64-6.85 (m, 1H) 7.10 (dd, J=11.53, 8.48 Hz, 1H) 7.46 (d, J=9.16 Hz, 2H) 7.54-7.70 (m, 3H) 7.76 (d, J=2.71 Hz, 1H) 7.90-8.07 (m, 2H) 8.24 (s, 1H) 8.47 (d, J=2.03 Hz, 1H) 9.10 (s, 1H) 10.06 (s, 1H) 10.11 (s, 1H).

EXAMPLE 29

This example was prepared as described in EXAMPLE 1H by substituting 1-(4-aminophenyl)-3-(4-(2-hydroxyethyl)phenyl)urea and 12D, for 1G and 1F respectively. $^1$H NMR (300 MHz, DMSO-d$_6$) δ 2.66 (t, J=7.12 Hz, 2H), 3.57 (t, J=7.12 Hz, 2H), 7.12 (d, J=8.48 Hz, 2H), 7.35 (d, J=8.14 Hz, 2H), 7.45 (d, J=9.16 Hz, 2H), 7.55-7.64 (m, 3H), 7.80 (d, J=3.05 Hz, 1H), 7.99 (s, 1H), 8.39 (s, 1H), 8.61 (s, 1H), 8.69 (s, 1H), 10.14 (s, 1H), 10.24 (s, 1H).

EXAMPLE 30

This example was prepared as described in EXAMPLE 1H by substituting EXAMPLE 10B and 12D, for 1G and 1F respectively. $^1$H NMR (300 MHz, DMSO-d$_6$) δ 2.69 (s, 2H) 3.59 (s, 2H) 4.63 (s, 1H) 6.83 (s, 1H) 7.06-8.01 (m, 10H) 8.17 (s, 1H) 8.57 (s, 1H) 8.63 (s, 1H) 9.97 (s, 1H) 10.08 (s, 1H)

EXAMPLE 31

This example was prepared as described in EXAMPLE 1H by substituting 1-(4-aminophenyl)-3-(3-(hydroxymethyl)phenyl)urea and 12D for EXAMPLES 1G and 1F, respectively. $^1$H NMR (300 MHz, DMSO-d$_6$) δ 4.47 (s, 2H), 6.91 (d, J=7.46 Hz, 1H), 7.13-7.27 (m, 1H), 7.28-7.36 (m, 1H), 7.39-7.51 (m, 3H), 7.55-7.66 (m, 3H), 7.78 (d, J=3.05 Hz, 1H), 7.97 (s, 1H), 8.32 (s, 1H), 8.68 (d, J=2.03 Hz, 2H), 10.12 (s, 1H) 10.16 (s, 1H).

EXAMPLE 32A

A solution of 1-(3-hydroxyphenyl)-3-(4-nitrophenyl)urea (1.37 g), Cs2CO3 (3.25 g), 3-bromopropan-1-ol (1.4 mL) in ethanol (30 mL) was refluxed for 30 hours, cooled to ambient temperature and partitioned between ethyl acetate and water. The organic extract was washed with 1N NaOH, brine, dried (MgSO$_4$), filtered and concentrated. A mixture of the concentrate and iron (2 g), NH$_4$Cl (0.29 g) in ethanol (10 mL)/water (10 mL) was refluxed for 24 hours, treated with 5 drops of 3N HCl and stirred at reflux for 3 hours. The mixture was cooled and filtered through diatomaceous earth (Celite®). The filtrate was extracted with ethyl acetate, and the extract was concentrated. The concentrate was triturated with boiling diethyl ether and filtered.

EXAMPLE 32B

This example was prepared as described in EXAMPLE 1H by substituting 32A and 12D, for 1G and 1F respectively. $^1$H NMR (300 MHz, DMSO-d$_6$) δ 1.77-1.94 (m, 2H) 3.50-3.62 (m, 2H) 4.01 (t, J=6.44 Hz, 2H) 4.53 (t, J=5.09 Hz, 1H) 6.54 (dd, J=8.14, 1.70 Hz, 1H) 6.89 (d, J=9.16 Hz, 1H) 7.16 (t, J=8.14 Hz, 1H) 7.22 (t, J=2.03 Hz, 1H) 7.44 (d, J=8.82 Hz, 2H) 7.56 (d, J=3.39 Hz, 1H) 7.61 (d, J=8.82 Hz, 2H) 7.74 (d, J=3.05 Hz, 1H) 7.93 (s, 1H) 8.16 (s, 1H) 8.63 (d, J=4.41 Hz, 2H) 9.99 (s, 1H) 10.07 (s, 1H).

EXAMPLE 33

This example was prepared as described in EXAMPLE 1H by substituting 1-(3-aminophenyl)-3-phenylurea and 12D, for 1G and 1F respectively. $^1$H NMR (300 MHz, DMSO-d$_6$) δ 6.97 (t, J=7.29 Hz, 1H) 7.19-7.36 (m, J=14.24, 6.78 Hz, 5H) 7.46 (d, J=7.80 Hz, 2H) 7.62 (d, J=3.05 Hz, 1H) 7.76 (d, J=3.05 Hz, 1H) 7.95 (s, 2H) 8.23 (s, 1H) 8.62 (s, 1H) 8.77 (s, 1H) 9.95 (s, 1H) 10.16 (s, 1H).

EXAMPLE 34

This example was prepared as described in EXAMPLE 1H by substituting 1-(3-aminophenyl)-3-m-tolylurea and 12D, for 1G and 1F respectively. $^1$H NMR (300 MHz, DMSO-d$_6$) δ 2.28 (s, 3H) 6.79 (d, J=7.46 Hz, 1H) 7.07-7.37 (m, 6H) 7.61 (d, J=3.05 Hz, 1H) 7.76 (d, J=3.05 Hz, 1H) 7.87-8.01 (m, 2H) 8.20 (s, 1H) 8.53 (s, 1H) 8.74 (s, 1H) 9.94 (s, 1H) 10.13 (s, 1H).

EXAMPLE 35

This example was prepared as described in EXAMPLE 1H by substituting 2-(2-aminothiazol-5-yl)-N-(3-fluorophenyl)acetamide and 12D, for 1G and 1F respectively. $^1$H NMR (500 MHz, DMSO-d$_6$) δ 3.90 (s, 2H) 6.80-6.98 (m, 1H) 7.23-7.47 (m, 3H) 7.61 (d, J=11.60 Hz, 1H) 7.78 (s, 2H) 7.99 (s, 1H) 8.33 (s, 1H) 9.66 (s, 1H) 10.46 (s, 1H) 12.43 (s, 1H).

EXAMPLE 36A

A solution of 3-(morpholinomethyl)aniline (0.46 g), TEA (0.37 mL) and 4-nitrophenyl carbonochloridate (530 mg) in THF (18 mL) was stirred at ambient temperature for 2 hours, treated with tert-butyl 4-aminophenylcarbamate (500 mg) and an additional 0.37 mL of TEA. the resulting mixture was stirred at ambient temperature for 48 hours, poured into water and extracted 3× with ethyl acetate. The extract was washed with brine, dried (MgSO$_4$), filtered and concentrated. The concentrate was purified by flash chromatography on silica gel with 2% methanol/dichloromethane to provide 1-(3-(morpholinomethyl)phenyl)-3-(4-nitrophenyl)urea which was dissolved in dichloromethane (30 mL), cooled in an ice bath, and treated with TFA (1.8 mL). The reaction mixture was stirred for 30 minutes at 0° C. and for 12 hours at ambient temperature, and concentrated three times from methanol/toluene.

EXAMPLE 36B

This example was prepared as described in EXAMPLE 1H by substituting 36A and 12D, for 1G and 1F respectively. $^1$H NMR (300 MHz, DMSO-d$_6$) δ 2.31-2.40 (m, 4H) 3.43 (s, 2H) 3.52-3.62 (m, 4H) 6.90 (d, J=7.46 Hz, 1H) 7.22 (t, J=7.63 Hz, 1H) 7.34 (d, J=9.15 Hz, 1H) 7.41-7.50 (m, 3H) 7.53-7.64 (m, 3H) 7.75 (d, J=3.05 Hz, 1H) 7.93 (s, 1H) 8.17 (s, 1H) 8.62 (s, 1H) 8.66 (s, 1H) 10.00 (s, 1H) 10.08 (s, 1H).

EXAMPLE 37A

The title compound was prepared by first substituting tert-butyl 4-aminobenzylcarbamate and 12D for EXAMPLES 1G and 1F respectively, in EXAMPLE 1H, removing the Nboc protecting group as described in EXAMPLE 1G.

EXAMPLE 37B

A mixture of EXAMPLE 37A (0.1 mmol) and TEA (0.2 mmol) in dichloromethane at −20° C. (3 mL) was treated with 1-isocyanato-3-methylbenzene (0.1 mmol), stirred at ambient temperature for 1 hour, and filtered. $^1$H NMR (300 MHz, DMSO-d$_6$) δ 2.24 (s, 3H) 4.23-4.39 (m, 2H) 6.56 (t, J=5.59 Hz, 1H) 6.71 (d, J=6.78 Hz, 1H) 7.01-7.35 (m, 5H) 7.53-7.82 (m, 4H) 7.94 (s, 1H) 8.19 (s, 1H) 8.45 (s, 1H) 9.93 (s, 1H) 10.13 (s, 1H).

EXAMPLE 38

This example was prepared as described in EXAMPLE 37B by substituting 1-fluoro-3-isocyanatobenzene for 1-isocyanato-3-methylbenzene. $^1$H NMR (300 MHz, DMSO-d$_6$) δ 4.29 (d, J=5.43 Hz, 2H) 6.43-6.83 (m, 2H) 7.05 (d, J=7.80 Hz, 1H) 7.15-7.36 (m, 3H) 7.41-7.81 (m, 5H) 7.94 (s, 1H) 8.19 (s, 1H) 8.80 (s, 1H) 9.93 (s, 1H) 10.13 (s, 1H).

EXAMPLE 39

This example was prepared as described in EXAMPLE 37 by substituting tert-butyl 3-aminobenzylcarbamate for tert-butyl 4-aminobenzylcarbamate in 37A and 1-fluoro-3-isocyanatobenzene for 1-isocyanato-3-methylbenzene in EXAMPLE 37B. 4 $^1$H NMR (400 MHz, DMSO-d$_6$) δ 4.32 (d, J=5.22 Hz, 2H) 6.62-6.81 (m, 2H) 7.01-7.13 (m, 2H) 7.18-7.37 (m, 2H) 7.48 (d, J=11.97 Hz, 1H) 7.55-7.71 (m, 3H) 7.75 (s, 1H) 7.95 (s, 1H) 8.22 (s, 1H) 8.85 (s, 1H) 9.92 (s, 1H) 10.17 (s, 1H).

EXAMPLE 40

This example was prepared as described in EXAMPLE 37 by substituting tert-butyl 3-aminobenzylcarbamate for tert-butyl 4-aminobenzylcarbamate in 37A and isocyanatobenzene for 1-isocyanato-3-methylbenzene in EXAMPLE 37B. $^1$H NMR (500 MHz, DMSO-d$_6$) δ 4.32 (d, J=5.80 Hz, 2H) 6.63 (t, J=5.65 Hz, 1H) 6.89 (t, J=7.17 Hz, 1H) 7.08 (d, J=7.32 Hz, 1H) 7.22 (t, J=7.63 Hz, 2H) 7.26-7.47 (m, 3H) 7.53-7.78 (m, 4H) 7.94 (s, 1H) 8.19 (s, 1H) 8.56 (s, 1H) 9.92 (s, 1H) 10.16 (s, 1H).

EXAMPLE 41

4-amino-N-(3-(((((4-(trifluoromethyl)phenyl)amino) carbonyl)amino)methyl)phenyl)pyrrolo[2,1-f][2,1,4] triazine-5-carboxamide The title compound was prepared by substituting tert-butyl 3-(aminomethyl)phenylcarbamate and 4-trifluoromethyl-isocyanatobenzene for (4-aminophenyl)carbamic acid tert-butyl ester and 1-fluoro-3-isocyanatobenzene, respectively in EXAMPLE 1G, then reacting the product with EXAMPLE 12D as described in EXAMPLE 1H. $^1$H NMR (300 MHz, DMSO-d$_6$) δ ppm 4.34 (d, J=5.55 Hz, 2H) 6.84 (t, J=5.95 Hz, 1H) 7.10 (d, J=7.54 Hz, 1H) 7.34 (t, J=7.93 Hz, 1H) 7.49-7.76 (m, 7H) 7.82 (d, J=2.78 Hz, 1H) 8.01 (s, 1H) 8.50 (s, 1H) 9.05 (s, 1H) 10.24 (s, 2H). MS (ESI(+)) m/e 470 (M+H)$^+$.

EXAMPLE 42

4-amino-N-(3-(((((3,4-difluorophenyl)amino)carbonyl)amino)methyl)phenyl)pyrrolo[2,1-f][2,1,4]triazine-5-carboxamide The title compound was prepared by substituting tert-butyl 3-(aminomethyl)phenylcarbamate and 1,2-difluoromethyl-4-isocyanatobenzene for (4-aminophenyl)carbamic acid tert-butyl ester and 1-fluoro-3-isocyanatobenzene, respectively in EXAMPLE 1G, then reacting the product with EXAMPLE 12D as described in EXAMPLE 1H. $^1$H NMR (300 MHz, DMSO-d$_6$) δ ppm 4.32 (d, J=5.55 Hz, 2H) 6.77 (t, J=5.75 Hz, 1H) 6.94-7.17 (m, 2H) 7.20-7.45 (m, 2H) 7.51-7.75 (m, 4H) 7.82 (d, J=3.17 Hz, 1H) 8.02 (s, 1H) 8.52 (s, 1H) 8.85 (s, 1H) 10.24 (s, 2H) MS (ESI(+)) m/e 438 (M+H)$^+$.

EXAMPLE 43

4-amino-N-(3-(((((4-chloro-2-fluorophenyl)amino) carbonyl)amino)methyl)phenyl)pyrrolo[2,1-f][2,1,4] triazine-5-carboxamide The title compound was prepared by substituting tert-butyl 3-(aminomethyl)phenylcarbamate and 4-chloro-2-fluoro-1-isocyanatobenzene for (4-aminophenyl)carbamic acid tert-butyl ester and 1-fluoro-3-isocyanatobenzene, respectively in EXAMPLE 1G, then reacting the product with EXAMPLE 12D as described in EXAMPLE 1H. $^1$H NMR (300 MHz, DMSO-d$_6$) δ ppm 4.33 (d, J=5.95 Hz, 2H) 7.03-7.24 (m, 3H) 7.28-7.48 (m, 2H) 7.53-7.73 (m, 3H) 7.79 (d, J=3.17 Hz, 1H) 7.98 (s, 1H) 8.17 (t, J=8.92 Hz, 1H) 8.35 (s, 1H) 8.51 (d, J=2.38 Hz, 1H) 10.07 (s, 1H) 10.20 (s, 1H). MS (ESI(+)) m/e 454 (M+H)$^+$.

EXAMPLE 44

4-amino-N-(3-(((((3-chlorophenyl)amino)carbonyl) amino)methyl)phenyl)pyrrolo[2,1-f][2,1,4]triazine-5-carboxamide The title compound was prepared by substituting tert-butyl 3-(aminomethyl)phenylcarbamate and 3-chloro-1-isocyanatobenzene for (4-aminophenyl)carbamic acid tert-butyl ester and 1-fluoro-3-isocyanatobenzene, respectively in EXAMPLE 1G, then reacting the product with EXAMPLE 12D as described in EXAMPLE 1H. $^1$H NMR (300 MHz, DMSO-d$_6$) δ ppm 4.32 (d, J=5.95 Hz, 2H) 6.77 (t, J=5.95 Hz, 1H) 6.85-7.00 (m, 1H) 7.02-7.44 (m, 4H) 7.52-7.75 (m, 4H) 7.82 (d, J=3.17 Hz, 1H) 8.01 (s, 1H) 8.48 (s, 1H) 8.82 (s, 1H) 10.23 (s, 2H) MS (ESI(+)) m/e 436 (M+H)+

EXAMPLE 45

4-amino-N-(3-(((((4-methylphenyl)amino)carbonyl) amino)methyl)phenyl)pyrrolo[2,1-f][2,1,4]triazine-5-carboxamide The title compound was prepared by substituting tert-butyl 3-(aminomethyl)phenylcarbamate and 1-isocyanato-4-methylbenzene for (4-aminophenyl)carbamic acid tert-butyl ester and 1-fluoro-3-isocyanatobenzene, respectively in EXAMPLE 1G, then reacting the product with EXAMPLE 12D as described in EXAMPLE 1H. $^1$H NMR (300 MHz, DMSO-d$_6$) δ ppm 2.21 (s, 3H) 4.31 (d, J=5.55 Hz, 2H) 6.58 (t, J=5.75 Hz, 1H) 6.93-7.15 (m, 3H) 7.21-7.40 (m, 3H) 7.52-7.74 (m, 3H) 7.81 (d, J=3.17 Hz, 1H) 8.01 (s, 1H) 8.44 (s, 1H) 8.48 (s, 1H) 10.23 (s, 2H). MS (ESI(+)) m/e 416 (M+H)$^+$.

EXAMPLE 46

4-amino-N-(3-(((((4-chlorophenyl)amino)carbonyl) amino)methyl)phenyl)pyrrolo[2,1-f][2,1,4]triazine-5-carboxamide The title compound was prepared by substituting tert-butyl 3-(aminomethyl)phenylcarbamate and 4-chloro-1-isocyanatobenzene for (4-aminophenyl)carbamic acid tert-butyl ester and 1-fluoro-3-isocyanatobenzene, respectively in EXAMPLE 1G, then reacting the product with EXAMPLE 12D as described in EXAMPLE 1H. $^1$H NMR (300 MHz, DMSO-d$_6$) δ ppm 4.32 (d, J=5.76 Hz, 2H) 6.70 (t, J=5.76 Hz, 1H) 7.09 (d, J=7.46 Hz, 1H) 7.18-7.51 (m, 5 H) 7.54-7.75 (m, 3H) 7.81 (d, J=3.05 Hz, 1H) 8.01 (s, 1H) 8.48 (d, J=2.03 Hz, 1H) 8.74 (s, 1H) 10.22 (s, 2H). MS (ESI(+)) m/e 436 (M+H)$^+$.

EXAMPLE 47

4-amino-N-(3-(((((4-fluorophenyl)amino)carbonyl)amino)methyl)phenyl)pyrrolo[2,1-f][2,1,4]triazine-5-carboxamide The title compound was prepared by substituting tert-butyl 3-(aminomethyl)phenylcarbamate and 4-fluoro-1-isocyanatobenzene for (4-aminophenyl)carbamic acid tert-butyl ester and 1-fluoro-3-isocyanatobenzene, respectively in EXAMPLE 1G, then reacting the product with EXAMPLE 12D as described in EXAMPLE 1H. $^1$H NMR (300 MHz, DMSO-d$_6$) δ ppm 4.32 (d, J=5.76 Hz, 2H) 6.64 (t, J=5.93 Hz, 1H) 6.97-7.15 (m, 3H) 7.26-7.47 (m, 3H) 7.57-7.71 (m, 3H) 7.82 (d, J=3.05 Hz, 1H) 8.01 (s, 1H) 8.49 (s, 1H) 8.61 (s, 1H) 10.23 (s, 2H). MS (ESI(+)) m/e 420 (M+H)$^+$.

EXAMPLE 48

4-amino-N-(3-(((((pyridin-3-ylamino)carbonyl)amino)methyl)phenyl)pyrrolo[2,1-f][2,1,4]triazine-5-carboxamide The title compound was prepared by substituting tert-butyl 3-(aminomethyl)phenylcarbamate and 3-isocyanatopyridine for (4-aminophenyl)carbamic acid tert-butyl ester and 1-fluoro-3-isocyanatobenzene, respectively in EXAMPLE 1G, then reacting the product with EXAMPLE 12D as described in EXAMPLE 1H. $^1$H NMR (300 MHz, DMSO-d$_6$) δ ppm 4.36 (d, J=5.76 Hz, 2H) 7.10 (d, J=8.14 Hz, 1H) 7.21-7.49 (m, 2H) 7.51-7.88 (m, 5H) 7.99 (s, 1H) 8.14-8.31 (m, 1H) 8.39 (d, J=5.09 Hz, 2H) 9.01 (d, J=2.37 Hz, 1H) 9.58 (s, 1H) 10.07 (s, 1H) 10.20 (s, 1H). MS (ESI(+)) m/e 403 (M+H)$^+$.

EXAMPLE 49

4-amino-N-(3-(((((4-(difluoromethoxy)phenyl)amino)carbonyl)amino)methyl)phenyl)pyrrolo[2,1-f][2,1,4]triazine-5-carboxamide The title compound was prepared by substituting tert-butyl 3-(aminomethyl)phenylcarbamate and 4-difluoromethoxy-1-isocyanatobenzene for (4-aminophenyl)carbamic acid tert-butyl ester and 1-fluoro-3-isocyanatobenzene, respectively in EXAMPLE 1G, then reacting the product with EXAMPLE 12D as described in EXAMPLE 1H. $^1$H NMR (300 MHz, DMSO-d$_6$) δ 4.31 (d, J=5.76 Hz, 2H) 6.66 (t, J=5.93 Hz, 1H) 6.84 (s, 1H) 6.98-7.20 (m, 3H) 7.19-7.86 (m, 7H) 7.94 (s, 1H) 8.23 (s, 1H) 8.68 (s, 1H) 9.93 (s, 1H) 10.17 (s, 1H) MS (ESI(+)) m/e 468 (M+H)$^+$.

EXAMPLE 50

4-amino-N-(3-(((((2,4-difluorophenyl)amino)carbonyl)amino)methyl)phenyl)pyrrolo[2,1-f][2,1,4]triazine-5-carboxamide The title compound was prepared by substituting tert-butyl 3-(aminomethyl)phenylcarbamate and 2,4-difluoro-1-isocyanatobenzene for (4-aminophenyl)carbamic acid tert-butyl ester and 1-fluoro-3-isocyanatobenzene, respectively in EXAMPLE 1G, then reacting the product with EXAMPLE 12D as described in EXAMPLE 1H. $^1$H NMR (300 MHz, DMSO-d$_6$) δ ppm 4.33 (d, J=5.76 Hz, 2H) 6.86-7.13 (m, 3H) 7.14-7.43 (m, 2H) 7.56-7.82 (m, 4H) 7.94 (s, 1H) 7.95-8.14 (m, 1H) 8.21 (s, 1H) 8.36 (d, J=2.03 Hz, 1H) 9.92 (d, J=5.09 Hz, 1H) 10.16 (s, 1H). MS (ESI(+)) m/e 438 (M+H)$^+$.

EXAMPLE 51

4-amino-N-(3-(((((2,5-difluorophenyl)amino)carbonyl)amino)methyl)phenyl)pyrrolo[2,1-f][2,1,4]triazine-5-carboxamide The title compound was prepared by substituting tert-butyl 3-(aminomethyl)phenylcarbamate and 1,4-difluoro-2-isocyanatobenzene for (4-aminophenyl)carbamic acid tert-butyl ester and 1-fluoro-3-isocyanatobenzene, respectively in EXAMPLE 1G, then reacting the product with EXAMPLE 12D as described in EXAMPLE 1H. $^1$H NMR (300 MHz, DMSO-d$_6$) δ ppm 4.34 (d, J=5.76 Hz, 2H) 6.52-6.83 (m, 1H) 6.97-7.44 (m, 4H) 7.54-7.82 (m, 4H) 7.94 (s, 1H) 8.00-8.11 (m, 1H) 8.20 (s, 1H) 8.63 (s, 1H) 9.91 (s, 1H) 10.16 (s, 1H). MS (ESI(+)) m/e 438 (M+H)$^+$.

EXAMPLE 52

4-amino-N-(4-((((4-chloro-2-fluorophenyl)amino)carbonyl)amino)phenyl)pyrrolo[2,1-f][2,1,4]triazine-5-carboxamide The title compound was prepared as described in EXAMPLES 1G-1H by substituting 4-chloro-2-fluoro-1-isocyanatobenzene for 1-fluoro-3-isocyanatobenzene in EXAMPLE 1G and EXAMPLE 12D for EXAMPLE 1F in EXAMPLE 1H. $^1$H NMR (300 MHz, DMSO-d$_6$) δ ppm 7.23 (d, J=9.16 Hz, 1H) 7.36-7.68 (m, 6H) 7.75 (d, J=3.05 Hz, 1H) 7.93 (s, 1H) 8.19 (t, J=8.82 Hz, 2H) 8.62 (s, 1H) 9.08 (s, 1H) 9.97 (s, 1H) 10.09 (s, 1H). MS (ESI(+)) m/e 440 (M+H)$^+$.

EXAMPLE 53

4-amino-N-(4-((((4-(trifluoromethyl)phenyl)amino)carbonyl)amino)phenyl)pyrrolo[2,1-f][2,1,4]triazine-5-carboxamide The title compound was prepared as described in EXAMPLES 1G-1H by substituting 4-trifluoromethyl-1-isocyanatobenzene for 1-fluoro-3-isocyanatobenzene in EXAMPLE 1G and EXAMPLE 12D for EXAMPLE 1F in EXAMPLE 1 H. $^1$H NMR (300 MHz, DMSO-d$_6$) δ ppm 7.41-7.72 (m, 9H) 7.75 (d, J=3.05 Hz, 1H) 7.94 (s, 1H) 8.17 (s, 1H) 8.80 (s, 1H) 9.08 (s, 1H) 9.98 (s, 1H) 10.09 (s, 1H). MS (ESI(+)) m/e 456 (M+H)$^+$.

EXAMPLE 54

8-amino-3-cyclopropyl-N-(4-((((3-fluorophenyl)amino)carbonyl)amino)phenyl)imidazo[1,5-a]pyrazine-1-carboxamide

EXAMPLE 54A 8-amino-3-cyclopropylimidazo[1,5-a]pyrazine-1-carboxylic acid

The title compound was prepared as described in EXAMPLES 1A-1F, by substituting cyclopropanecarboxylic acid for acetic acid in 1A.

EXAMPLE 54B 8-amino-3-cyclopropyl-N-(4-((((3-fluorophenyl)amino)carbonyl)amino)phenyl)imidazo[1,5-a]pyrazine-1-carboxamide The title compound was prepared as described in EXAMPLES 1H, except substituting EXAMPLE 54A for EXAMPLE 1F. $^1$H NMR (300 MHz, DMSO-$d_6$) δ ppm 0.87-1.28 (m, 4H) 2.19-2.45 (m, 1H) 6.60-6.91 (m, 1H) 7.04-7.59 (m, 7H) 7.58-7.90 (m, 3H) 8.74 (s, 1H) 8.90 (s, 1H) 9.21 (s, 1H) 9.96 (s, 1H). MS (ESI(+)) m/e 446 (M+H)$^+$.

EXAMPLE 55

8-amino-N-(4-((anilinocarbonyl)amino)phenyl)-3-cyclopropylimidazo[1,5-a]pyrazine-1-carboxamide The title compound was prepared as described in EXAMPLES 1G-1H by substituting isocyanatobenzene for 1-fluoro-3-isocyanatobenzene in EXAMPLE 1G and EXAMPLE 54A for EXAMPLE 1F in EXAMPLE 1H. $^1$H NMR (300 MHz, DMSO-$d_6$) δ ppm 0.87-1.32 (m, 4H) 2.15-2.42 (m, 1H) 6.96 (t, J=7.29 Hz, 1H) 7.11-7.59 (m, 8H) 7.59-7.86 (m, 3H) 8.64 (d, J=2.03 Hz, 2H) 9.17 (s, 1H) 9.94 (s, 1H). MS (ESI(+)) m/e 428 (M+H)$^+$.

EXAMPLE 56

8-amino-3-cyclopropyl-N-(4-((((3-methylphenyl)amino)carbonyl)amino)phenyl)imidazo[1,5-a]pyrazine-1-carboxamide The title compound was prepared as described in EXAMPLES 1G-1H by substituting 1-isocyanato-3-methylbenzene for 1-fluoro-3-isocyanatobenzene in EXAMPLE 1G and EXAMPLE 54A for EXAMPLE 1F in EXAMPLE 1H. $^1$H NMR (300 MHz, DMSO-$d_6$) δ ppm 0.85-1.41 (m, 4H) 2.28 (s, 3H) 2.29-2.45 (m, 1H) 6.78 (d, J=7.14 Hz, 1H) 7.00-7.54 (m, 7H) 7.59-7.85 (m, 3H) 8.57 (s, 1H) 8.64 (s, 1H) 9.15 (s, 1H) 9.94 (s, 1H). MS (ESI(+)) m/e 442 (M+H)$^+$.

EXAMPLE 57

8-amino-3-cyclopropyl-N-(4-(((((2-fluoro-5-(trifluoromethyl)phenyl)amino)carbonyl)amino)phenyl)imidazo[1,5-a]pyrazine-1-carboxamide The title compound was prepared as described in EXAMPLES 1G-1H by substituting 1-fluoro-2-isocyanato-4-(trifluoromethyl)benzene for 1-fluoro-3-isocyanatobenzene in EXAMPLE 1G and EXAMPLE 54A for EXAMPLE 1F in EXAMPLE 1H. $^1$H NMR (300 MHz, DMSO-$d_6$) δ ppm 0.84-1.29 (m, 4H) 2.16-2.45 (m, 1H) 7.20 (d, J=3.73 Hz, 1H) 7.30-7.64 (m, 5H) 7.66-8.03 (m, 3H) 8.63 (dd, J=7.29, 2.20 Hz, 1H) 8.87 (d, J=2.71 Hz, 1H) 9.16 (s, 2H) 9.98 (s, 1H). MS (ESI(+)) m/e 514 (M+H)$^+$.

EXAMPLE 58

8-amino-3-cyclopropyl-N-(4-(((((4-(trifluoromethyl)phenyl)amino)carbonyl)amino)phenyl)imidazo[1,5-a]pyrazine-1-carboxamide The title compound was prepared as described in EXAMPLES 1G-1H by substituting 1-isocyanato-4-(trifluoromethyl)benzene for 1-fluoro-3-isocyanatobenzene in EXAMPLE 1G and EXAMPLE 54A for EXAMPLE 1F in EXAMPLE 1H. $^1$H NMR (300 MHz, DMSO-$d_6$) δ ppm 1.01-1.33 (m, 4H) 2.46-2.62 (m, 1H) 7.22 (d, J=5.52 Hz, 1H) 7.50 (d, J=8.90 Hz, 2H) 7.56-7.81 (m, 6H) 7.99 (d, J=5.83 Hz, 1H) 8.99 (s, 1H) 9.24 (s, 2H) 10.33 (s, 1H) 10.92 (s, 1H). MS (ESI(+)) m/e 496 (M+H)$^+$.

EXAMPLE 59

8-amino-3-cyclopropyl-N-(3-(((((pyridin-3-ylamino)carbonyl)amino)methyl)phenyl)imidazo[1,5-a]pyrazine-1-carboxamide The title compound was prepared as described in EXAMPLES 1G-1H by substituting 3-isocyanatopyridine for 1-fluoro-3-isocyanatobenzene in EXAMPLE 1G and EXAMPLE 54A for EXAMPLE 1F in EXAMPLE 1H. $^1$H NMR (400 MHz, DMSO-$d_6$) δ ppm 1.16 (s, 4H) 2.22-2.43 (m, 1H) 6.93-8.01 (m, 9H) 8.20 (s, 1H) 8.64 (s, 1H) 9.01 (d, J=19.03 Hz, 2H) 10.14 (s, 2H). MS (ESI(+)) m/e 429 (M+H)$^+$.

EXAMPLE 60

8-amino-3-cyclopropyl-N-(4-((((3-fluorophenyl)amino)carbonyl)amino)-3-methylphenyl)imidazo[1,5-a]pyrazine-1-carboxamide The title compound was prepared as described in EXAMPLES 1G-1H by substituting tert-butyl 4-amino-3-methylphenylcarbamate for (4-aminophenyl)carbamic acid tert-butyl ester in EXAMPLE 1G and EXAMPLE 54A for EXAMPLE 1F in EXAMPLE 1H. $^1$H NMR (300 MHz, DMSO-$d_6$) δ ppm 1.01-1.15 (m, 4H) 2.26 (s, 3H) 2.29-2.41 (m, 1H) 6.63-6.85 (m, 1H) 7.10 (d, J=7.54 Hz, 1H) 7.20 (d, J=4.76 Hz, 1H) 7.24-7.36 (m, 1H) 7.46-7.62 (m, 2H) 7.62-7.76 (m, 3H) 7.98 (s, 1H) 9.17 (s, 1H) 9.90 (s, 1H). MS (ESI(+)) m/e 460 (M+H)$^+$.

EXAMPLE 61

8-amino-3-cyclopropyl-N-(4-((((2-fluorophenyl)amino)carbonyl)amino)-3-methylphenyl)imidazo[1,5-a]pyrazine-1-carboxamide The title compound was prepared as described in EXAMPLES 1G-1H by substituting 1-fluoro-2-isocyanatobenzene and tert-butyl 4-amino-3-methylphenylcarbamate for 1-fluoro-3-isocyanatobenzene and (4-aminophenyl)carbamic acid tert-butyl ester, respectively in EXAMPLE 1G and EXAMPLE 54A for EXAMPLE 1F in EXAMPLE 1H. $^1$H NMR (300 MHz, DMSO-$d_6$) δ μm 0.98-1.30 (m, 4H) 2.10-2.37 (m, 4H) 6.88-7.34 (m, 4H) 7.52-7.70 (m, 2H) 7.75-7.90 (m, 1H) 7.93-8.06 (m, 1H) 8.11-8.27 (m, 1H) 8.28-8.49 (m, 1H) 8.71-9.26 (m, 2H) 10.24 (s, 1H) 10.77 (s, 1H). MS (ESI(+)) m/e 460 (M+H)$^+$.

EXAMPLE 62

8-amino-3-cyclopropyl-N-(3-methyl-4-((((4-(trifluoromethyl)phenyl)amino)carbonyl)amino)phenyl)imidazo[1,5-a]pyrazine-1-carboxamide The title compound was prepared as described in EXAMPLES 1G-1H by substituting 1-isocyanato-4-trifluoromethylbenzene and tert-butyl 4-amino-3-methylphenylcarbamate for 1-fluoro-3-isocyanatobenzene and (4-aminophenyl)carbamic acid tert-butyl ester, respectively in EXAMPLE 1G and EXAMPLE 54A for EXAMPLE 1F in EXAMPLE 1H. $^1$H NMR (300 MHz, DMSO-d$_6$) δ ppm 0.96-1.30 (m, 4H) 2.04-2.37 (m, 4H) 7.02-7.34 (m, 1H) 7.51-7.83 (m, 7H) 7.89-8.04 (m, 1H) 8.13 (s, 1H) 9.11 (s, 1H) 9.44 (s, 1H) 10.27 (s, 1H) 10.84 (s, 1H). MS (ESI(+)) m/e 510 (M+H)$^+$.

EXAMPLE 63

8-amino-3-cyclopropyl-N-(3-(((((3-fluorophenyl) amino)carbonyl)amino)phenyl)imidazo[1,5-a]pyrazine-1-carboxamide The title compound was prepared as described in EXAMPLES 1G-1H by substituting (3-aminophenyl)carbamic acid tert-butyl ester for (4-aminophenyl)carbamic acid tert-butyl ester in EXAMPLE 1G and EXAMPLE 54A for EXAMPLE 1F in EXAMPLE 1H. $^1$H NMR (300 MHz, DMSO-d$_6$) δ ppm 0.80-1.26 (m, 4H) 2.14-2.45 (m, 1H) 6.50-6.87 (m, 1H) 7.05-7.60 (m, 8H) 7.74 (d, J=4.75 Hz, 1H) 8.00 (s, 1H) 8.83 (d, J=3.05 Hz, 2H) 9.15 (s, 1H) 9.96 (s, 1H). MS (ESI(+)) m/e 446 (M+H)$^+$.

EXAMPLE 64

8-amino-3-cyclopropyl-N-(3-(((((3-fluorophenyl) amino)carbonyl)amino)methyl)phenyl)imidazo[1,5-a]pyrazine-1-carboxamide The title compound was prepared as described in EXAMPLE 1G-H by substituting tert-butyl 3-(aminomethyl)phenylcarbamate for (4-aminophenyl)carbamic acid tert-butyl ester in EXAMPLE 1G and EXAMPLE 54A for EXAMPLE 1F in EXAMPLE 1H. $^1$H NMR (300 MHz, DMSO-d$_6$) δ ppm 0.86-1.28 (m, 4H) 2.16-2.44 (m, 1H) 4.31 (d, J=5.76 Hz, 2H) 6.47-6.90 (m, 2H) 6.94-7.55 (m, 7H) 7.57-7.97 (m, 3H) 8.82 (s, 1H) 9.16 (s, 1H) 10.01 (s, 1H). MS (ESI(+)) m/e 460 (M+H)$^+$.

EXAMPLE 65

8-amino-N-(3-(((((4-chloro-2-fluorophenyl)amino) carbonyl)amino)methyl)phenyl)-3-cyclopropylimidazo[1,5-a]pyrazine-1-carboxamide The title compound was prepared as described in EXAMPLE 1G-H by substituting tert-butyl 3-(aminomethyl)phenylcarbamate and 4-chloro-2-fluoro-1-isocyanatobenzene for (4-aminophenyl)carbamic acid tert-butyl ester and 1-fluoro-3-isocyanatobenzene, respectively in EXAMPLE 1G and EXAMPLE 54A for EXAMPLE 1F in EXAMPLE 1H. $^1$H NMR (300 MHz, DMSO-d$_6$) δ ppm 0.58-1.50 (m, 4H) 2.17-2.43 (m, 1H) 4.33 (d, J=5.76 Hz, 2H) 6.89-7.53 (m, 7H) 7.59-7.90 (m, 3H) 8.18 (t, J=8.98 Hz, 1H) 8.52 (d, J=2.03 Hz, 1H) 9.12 (s, 1H) 10.02 (s, 1H). MS (ESI(+)) m/e 494 (M+H)$^+$.

EXAMPLE 66

8-amino-N-(3-(((anilinocarbonyl)amino)methyl) phenyl)-3-cyclopropylimidazo[1,5-a]pyrazine-1-carboxamide The title compound was prepared as described in EXAMPLE 1G-H by substituting tert-butyl 3-(aminomethyl)phenylcarbamate and isocyanatobenzene for (4-aminophenyl)carbamic acid tert-butyl ester and 1-fluoro-3-isocyanatobenzene, respectively in EXAMPLE 1G and EXAMPLE 54A for EXAMPLE 1F in EXAMPLE 1H. $^1$H NMR (300 MHz, DMSO-d$_6$) δ ppm 0.84-1.33 (m, 4H) 2.14-2.44 (m, 1H) 4.31 (d, J=5.76 Hz, 2H) 6.62 (t, J=5.93 Hz, 1H) 6.89 (t, J=7.46 Hz, 1H) 7.07 (d, J=7.80 Hz, 1H) 7.15-7.53 (m, 7H) 7.54-8.00 (m, 3H) 8.54 (s, 1H) 9.06 (s, 1H) 10.00 (s, 1H). MS (ESI(+)) m/e 442 (M+H)$^+$.

EXAMPLE 67

8-amino-3-cyclopropyl-N-(3-(((((3,4-difluorophenyl) amino)carbonyl)amino)methyl)phenyl)imidazo[1,5-a]pyrazine-1-carboxamide The title compound was prepared as described in EXAMPLE 1G-H by substituting tert-butyl 3-(aminomethyl)phenylcarbamate and 3,4-difluoro-1-isocyanatobenzene for (4-aminophenyl)carbamic acid tert-butyl ester and 1-fluoro-3-isocyanatobenzene, respectively in EXAMPLE 1G and EXAMPLE 54A for EXAMPLE 1F in EXAMPLE 1H. $^1$H NMR (300 MHz, DMSO-d$_6$) δ ppm 0.82-1.41 (m, 4H) 2.21-2.44 (m, 1H) 4.31 (d, J=5.76 Hz, 2H) 6.73 (t, J=5.93 Hz, 1H) 6.90-7.13 (m, 1H) 7.14-7.46 (m, 5H) 7.50-7.95 (m, 4H) 8.81 (s, 1H) 9.20 (s, 1H) 10.00 (s, 1H). MS (ESI(+)) m/e 478 (M+H)$^+$.

EXAMPLE 68

8-amino-3-cyclopropyl-N-(3-(((((2-fluorophenyl) amino)carbonyl)amino)methyl)phenyl)imidazo[1,5-a]pyrazine-1-carboxamide

EXAMPLE 68A 8-amino-N-(3-(aminomethyl)phenyl)-3-cyclopropylimidazo[1,5-a]pyrazine-1-carboxamide The title compound was prepared as a bis-trifluoroaceate salt by first substituting tert-butyl 3-aminobenzylcarbamate and EXAMPLE 54A for EXAMPLES 1G and EXAMPLE 1F respectively, in EXAMPLE 1H, followed by removing the NBoc protecting group by treatment with TFA as described in EXAMPLE 1G. MS (ESI(+)) m/e 323 (M+H)$^+$.

EXAMPLE 68B 8-amino-3-cyclopropyl-N-(3-(((((2-fluorophenyl) amino)carbonyl)amino)methyl)phenyl)imidazo[1,5-a]pyrazine-1-carboxamide The title compound was prepared as described in EXAMPLE 37B by substituting 1-fluoro-2-isocyanatobenzene and EXAMPLE 68A for 1-isocyanato-3-methylbenzene and EXAMPLE 37A, respectively. $^1$H NMR (300 MHz, DMSO-d$_6$) δ ppm 1.13-1.41 (m, 4H) 2.36-2.63 (m, 1H) 4.34 (d, J=5.52 Hz, 2H) 6.94 (s, 1H) 7.01-7.29 (m, 5H) 7.37 (t, J=7.67 Hz, 1H) 7.57-7.85 (m, 2H) 7.99 (d, J=5.52 Hz, 1H) 8.06-8.28 (m, 1H) 8.39 (d, J=1.84 Hz, 1H) 9.26 (s, 1H) 10.39 (s, 1H) 10.83 (s, 1H)
MS (ESI(+)) m/e 460 (M+H)$^+$.

EXAMPLE 69

8-amino-3-cyclopropyl-N-(3-(((((4-fluorophenyl) amino)carbonyl)amino)methyl)phenyl)imidazo[1,5-a]pyrazine-1-carboxamide The title compound was prepared as described in EXAMPLE 37B by substituting 1-fluoro-4-isocyanatobenzene and EXAMPLE 68A for 1-isocyanato-3-methylbenzene and EXAMPLE 37A, respectively. $^1$H NMR (300 MHz, DMSO-$d_6$) δ ppm 1.07-1.36 (m, 4H) 2.38-2.60 (m, 1H) 4.32 (d, J=5.83 Hz, 2H) 6.73 (t, J=5.68 Hz, 1H) 6.94-7.56 (m, 7H) 7.58-7.89 (m, 2H) 7.99 (d, J=5.83 Hz, 1H) 8.68 (s, 1H) 9.33 (s, 1H) 10.37 (s, 1H) 10.82 (s, 1H).
MS (ESI(+)) m/e 460 (M+H)$^+$.

EXAMPLE 70

8-amino-N-(3-(((((3-chlorophenyl)amino)carbonyl) amino)methyl)phenyl)-3-cyclopropylimidazo[1,5-a] pyrazine-1-carboxamide The title compound was prepared as described in EXAMPLE 37B by substituting 1-chloro-3-isocyanatobenzene and EXAMPLE 68A for 1-isocyanato-3-methylbenzene and EXAMPLE 37A, respectively. $^1$H NMR (300 MHz, DMSO-$d_6$) δ ppm 1.13-1.33 (m, 4H) 2.31-2.49 (m, 1H) 4.32 (d, J=5.83 Hz, 2H) 6.82 (t, J=6.14 Hz, 1H) 6.89-7.01 (m, 1H) 7.06-7.27 (m, 4H) 7.36 (t, J=7.83 Hz, 1H) 7.52-7.86 (m, 3H) 7.97 (d, J=5.52 Hz, 1H) 8.86 (s, 1H) 9.09 (s, 1H) 10.35 (s, 1H) 10.69 (s, 1H). MS (ESI(+)) m/e 476 (M+H)$^+$.

EXAMPLE 71

8-amino-N-(3-(((((4-chlorophenyl)amino)carbonyl) amino)methyl)phenyl)-3-cyclopropylimidazo[1,5-a] pyrazine-1-carboxamide The title compound was prepared as described in EXAMPLE 37B by substituting 1-chloro-4-isocyanatobenzene and EXAMPLE 68A for 1-isocyanato-3-methylbenzene and EXAMPLE 37A, respectively. $^1$H NMR (300 MHz, DMSO-$d_6$) δ ppm 0.99-1.41 (m, 4H) 2.24-2.48 (m, 1H) 4.32 (d, J=5.76 Hz, 2H) 6.74 (t, J=5.76 Hz, 1H) 7.03-7.56 (m, 7H) 7.59-7.85 (m, 2H) 8.00 (d, J=5.76 Hz, 1H) 8.78 (s, 1H) 9.24 (s, 1H) 10.40 (s, 1H) 10.86 (s, 1H)
MS (ESI(+)) m/e 476 (M+H)$^+$.

EXAMPLE 72

8-amino-3-cyclopropyl-N-(4-(((pyridin-3-ylamino) carbonyl)amino)phenyl)imidazo[1,5-a]pyrazine-1-carboxamide The title compound was prepared as described in EXAMPLE 37B by substituting 3-isocyanatopyridine and EXAMPLE 68A for 1-isocyanato-3-methylbenzene and EXAMPLE 37A, respectively. $^1$H NMR (300 MHz, DMSO-$d_6$) δ ppm 0.79-1.39 (m, 4H) 2.17-2.43 (m, 1H) 4.33 (d, J=5.83 Hz, 2H) 6.80 (t, J=5.83 Hz, 1H) 6.95-7.56 (m, 5H) 7.57-7.84 (m, 3H) 7.82-8.00 (m, 1H) 8.12 (d, J=3.68 Hz, 1H) 8.55 (d, J=2.15 Hz, 1H) 8.77 (s, 1H) 9.05 (s, 1H) 10.00 (s, 1H) MS (ESI(+)) m/e 443 (M+H)$^+$.

EXAMPLE 73

8-amino-3-cyclopropyl-N-(3-(((phenylsulfonyl) amino)methyl)phenyl)imidazo[1,5-a]pyrazine-1-carboxamide A solution of EXAMPLE 68A (0.102 g) in DMF 3 mL was treated with triethylamine (0.112 ml, 0.800 mmol) and benzenesulfonyl chloride (0.026 ml, 0.200 mmol), stirred at room temperature overnight then diluted with water and extracted with ethyl acetate. The extract was washed (brine), dried (MgSO$_4$), concentrated to dryness and purified by preparative HPLC. $^1$H NMR (300 MHz, DMSO-$d_6$) δ ppm 1.01-1.29 (m, 4H) 2.34-2.58 (m, 1H) 3.98 (d, J=5.95 Hz, 2H) 7.04 (d, J=7.54 Hz, 1H) 7.19-7.36 (m, 2H) 7.48-7.69 (m, 4H) 7.72 (s, 1H) 7.77-7.91 (m, 2H) 7.98 (d, J=5.55 Hz, 1H) 8.18 (t, J=6.35 Hz, 1H) 9.08 (s, 1H) 10.32 (s, 1H) 10.69 (s, 1H). MS (ESI(+)) m/e 463 (M+H)$^+$.

EXAMPLE 74

8-amino-3-(3-(ethyl(2-hydroxyethyl)amino)-3-oxopropyl)-N-(3-(((((4-(trifluoromethyl)phenyl)amino) carbonyl)amino)methyl)phenyl)imidazo[1,5-a]pyrazine-1-carboxamide

EXAMPLE 74A

Ethyl 3-(8-chloro-1-iodoimidazo[1,5-a]pyrazin-3-yl)propanoate
The title compound was prepared as described in EXAMPLES 1A-1C, except substituting 4-ethoxy-4-oxobutanoic acid for acetic acid in EXAMPLE 1A. MS (ESI(+)) m/e 380 (M+H)$^+$.

EXAMPLE 74B 3-(8-chloro-1-iodoimidazo[1,5-a]pyrazin-3-yl)propanoic acid

A solution of EXAMPLE 74A (1.96 g) in tetrahydrofuran (5 mL) and ethanol (1 mL) was treated with 2N LiOH (5.16 ml), stirred at room temperature for 3 hours and then neutralized to pH 3-4 with 3N HCl. The mixture was extracted with ethyl acetate. The extract was washed (brine), dried (MgSO$_4$) and concentrated to dryness to give the title compound. MS (ESI(+)) m/e 352 (M+H)$^+$.

EXAMPLE 74C 3-(8-amino-1-iodoimidazo[1,5-a]pyrazin-3-yl)-N-ethyl-N-(2-hydroxyethyl)propanamide A mixture of EXAMPLE 74B (1.3 g), 2-(ethylamino)ethanol (0.363 g), 1-ethyl-3-(3-(dimethylamino)propyl)-carbodiimide hydrochloride (0.78 g), 1-hydroxybenzotriazole hydrate (0.623 g), and N-methylmorpholine (0.748 g) in 5 mL DMF was stirred at room temperature for 10 hours. The reaction mixture was extracted with ethyl acetate 3 times and the combined extracts were washed (brine), dried (MgSO$_4$) and concentrated. The residue was purified by flash chromatography with 0-4% methanol/CH$_2$Cl$_2$ to afford 3-(8-(1H-benzo(d)(1,2,3)triazol-1-yloxy)-1-iodoimidazo[1,5-a] pyrazin-3-yl)-N-ethyl-N-(2-hydroxyethyl)propanamide. MS (ESI(+)) m/e 522 (M+H)$^+$ This product was placed in a high pressure tube with 7N ammonia (15 ml) in methanol, heated at 60 C overnight then concentrated to dryness. The residue was purified by flash column with 0-10% methanol/CH$_2$Cl$_2$ to give the title compound. MS (ESI(+)) m/e 404 (M+H)$^+$

EXAMPLE 74D 8-amino-3-(3-(ethyl(2-hydroxyethyl)amino)-3-oxopropyl)imidazo[1,5-a]pyrazine-1-carboxylic acid The title compound was prepared as described in EXAMPLES 1E-1F, substituting EXAMPLE 74C for EXAMPLE 1D in EXAMPLE 1E.

EXAMPLE 74E 8-amino-3-(3-(ethyl(2-hydroxyethyl)amino)-3-oxo-propyl)-N-(3-(((((4-(trifluoromethyl)phenyl)amino)carbonyl)amino)methyl)phenyl)imidazo[1,5-a]pyrazine-1-carboxamide The title compound was prepared by substituting tert-butyl 3-(aminomethyl)phenylcarbamate and 4-trifluoromethyl-isocyanatobenzene for (4-aminophenyl)carbamic acid tert-butyl ester and 1-fluoro-3-isocyanatobenzene, respectively in EXAMPLE 1G, then reacting the product with EXAMPLE 74D as described in EXAMPLE 1H. $^1$H NMR (300 MHz, DMSO-$d_6$) δ ppm 0.70-1.45 (m, 3H) 2.86-3.15 (m, 2H) 3.09-3.92 (m, 8H) 4.34 (d, J=6.14 Hz, 2H) 6.86 (t, J=5.68 Hz, 1H) 7.12-7.27 (m, 2H) 7.37 (t, J=7.83 Hz, 1H) 7.52-7.71 (m, 5H) 7.77 (s, 1H) 7.89 (t, J=5.83 Hz, 1H) 9.06 (s, 2H) 10.45 (d, J=7.37 Hz, 1H) 10.74 (s, 1H).
MS (ESI(+)) m/e 613 (M+H)$^+$.

EXAMPLE 75

8-amino-N-(3-(((((4-chloro-2-fluorophenyl)amino)carbonyl)amino)methyl)phenyl)-3-(3-(ethyl(2-hydroxyethyl)amino)-3-oxopropyl)imidazo[1,5-a]pyrazine-1-carboxamide The title compound was prepared by substituting tert-butyl 3-(aminomethyl)phenylcarbamate and 4-chloro-2-fluoro-1-isocyanatobenzene for (4-aminophenyl)carbamic acid tert-butyl ester and 1-fluoro-3-isocyanatobenzene, respectively in EXAMPLE 1G, then reacting the product with EXAMPLE 74D as described in EXAMPLE 1H. $^1$H NMR (300 MHz, DMSO-$d_6$) δ ppm 0.73-1.40 (m, 3H) 2.84-3.89 (m, 10H) 4.26-4.45 (m, 2H) 4.86 (s, 1H) 7.00-7.54 (m, 6H) 7.55-7.97 (m, 3H) 8.17 (t, J=8.82 Hz, 1H) 8.52 (d, J=2.37 Hz, 1H) 9.04 (s, 1H) 10.47 (d, J=5.43 Hz, 1H) 10.70 (s, 1H). MS (ESI(+)) m/e 597 (M+H)$^+$.

EXAMPLE 76

8-amino-3-(3-(ethyl(2-hydroxyethyl)amino)-3-oxo-propyl)-N-(3-(((((3-fluorophenyl)amino)carbonyl)amino)methyl)phenyl)imidazo[1,5-a]pyrazine-1-carboxamide The title compound was prepared by substituting tert-butyl 3-(aminomethyl)phenylcarbamate for (4-aminophenyl)carbamic acid tert-butyl ester in EXAMPLE 1G, then reacting the product with EXAMPLE 74D as described in EXAMPLE 1H. $^1$H NMR (300 MHz, DMSO-$d_6$) δ ppm 0.84-1.30 (m, 3H) 2.82-4.00 (m, 10H) 4.27-4.42 (m, 2H) 4.87 (s, 1H) 6.53-6.87 (m, 2H) 6.96-7.56 (m, 6H) 7.59-8.01 (m, 3H) 8.87 (s, 1H) 9.12 (s, 1H) 10.47 (d, J=5.43 Hz, 1H) 10.76 (s, 1H). MS (ESI(+)) m/e 563 (M+H)$^+$.

EXAMPLE 77

8-amino-3-(3-(ethyl(2-hydroxyethyl)amino)-3-oxo-propyl)-N-(4-((((3-fluorophenyl)amino)carbonyl)amino)phenyl)imidazo[1,5-a]pyrazine-1-carboxamide The title compound was prepared as described in EXAMPLE 1H by substituting EXAMPLE 74D for EXAMPLE 1F. $^1$H NMR (300 MHz, DMSO-$d_6$) δ ppm 0.73-1.33 (m, 3H) 2.82-4.08 (m, 10H) 4.97 (s, 1H) 6.59-6.88 (m, 1H) 7.02-7.40 (m, 3H) 7.42-7.60 (m, 3H) 7.60-7.84 (m, 2H) 7.83-8.09 (m, 1H) 8.84 (s, 1H) 8.97 (s, 2H) 10.44 (d, J=2.71 Hz, 1H) 10.84 (s, 1H). MS (ESI(+)) m/e 549 (M+H)$^+$.

EXAMPLE 78

8-amino-3-cyclopropyl-N-(3-(((((4-(trifluoromethyl)phenyl)amino)carbonyl)amino)methyl)phenyl)imidazo[1,5-a]pyrazine-1-carboxamide The title compound was prepared as described in EXAMPLEs 1G-1H by substituting tert-butyl 3-(aminomethyl)phenylcarbamate and 1-isocyanato-4-trifluoromethyl-benzene for (4-aminophenyl)carbamic acid tert-butyl ester and 1-fluoro-3-isocyanatobenzene, respectively in EXAMPLE 1G and EXAMPLE 54A for EXAMPLE 1F in EXAMPLE 1H.
$^1$H NMR (300 MHz, DMSO-$d_6$) δ ppm 0.89-1.28 (m, 4H) 2.17-2.42 (m, 1H) 4.33 (d, J=5.55 Hz, 2H) 6.81 (t, J=5.75 Hz, 1H) 7.08 (d, J=7.93 Hz, 1H) 7.20 (d, J=5.16 Hz, 1H) 7.32 (t, J=7.93 Hz, 1H) 7.45-7.93 (m, 7H) 9.02 (s, 1H) 10.01 (s, 1H). MS (ESI(+)) m/e 510 (M+H)$^+$.

The foregoing is meant to illustrate the invention but not to limit it. Variations and changes obvious to one skilled in the art are intended to be within the scope of the invention as defined in the claims.

We claim:
1. A compound having Formula I

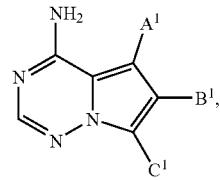

(I)

or a therapeutically acceptable salt thereof, wherein
$A^1$ is C(O)NHR$^1$;
$B^1$ and $C^1$ are independently H; wherein
$R^1$ is $R^2$ or $R^3$;
$R^2$ is phenyl;
$R^3$ is heteroaryl;
wherein $R^2$ and $R^3$ are substituted with NHC(O)R$^{30}$, NHC(O)NHR$^{30}$, or alkyl which is substituted with C(O)NHR$^{35}$ or NHC(O)NHR$^{35}$;
$R^{30}$ is $R^{31}$, $R^{32}$ or $R^{33}$;
$R^{31}$ is phenyl;
$R^{32}$ is heteroaryl;
$R^{33}$ is cycloalkyl;
$R^{35}$ is $R^{36}$ or $R^{37}$;
$R^{36}$ is phenyl;
$R^{37}$ is heteroaryl;
wherein the moieties represented by $R^{31}$ and $R^{36}$ are independently unsubstituted or substituted with one or two of independently selected F, Cl, Br, I, CF$_3$, OCF$_2$, R$^{45}$, or OR$^{45}$;
$R^{45}$ is alkyl which is unsubstituted or substituted with R$^{50}$, F, Cl, Br, I, or OH; and
$R^{50}$ is heterocycloalkyl.
2. The compound of claim 1, wherein $R^1$ is $R^2$.
3. The compound of claim 2, wherein $R^2$ is substituted with NHC(O)NHR$^{30}$.
4. The compound of claim 2, wherein $R^2$ is substituted with alkyl which is substituted with NHC(O)NHR$^{35}$.

5. The compound of claim 1, wherein $R^1$ is $R^3$.

6. The compound of claim 2, wherein $R^3$ is substituted with NHC(O)NHR$^{30}$.

7. The compound of claim 2, wherein $R^3$ is substituted with alkyl which is substituted with NHC(O)NHR$^{35}$.

8. The compound of claim 1 selected from the group consisting of 4-amino-N-(4-((((3-fluorophenyl)amino)carbonyl)amino)phenyl)pyrrolo[2,1-f][2,1,4]triazine-5-carboxamide, 4-amino-N-(4-((((4-fluorophenyl)amino)carbonyl)amino)phenyl)pyrrolo[2,1-f][2,1,4]triazine-5-carboxamide, 4-amino-N-(4-((((2-fluorophenyl)amino)carbonyl)amino)phenyl)pyrrolo[2,1-f][2,1,4]triazine-5-carboxamide, 4-amino-N-(4-((anilinocarbonyl)amino)phenyl)pyrrolo[2,1-f][2,1,4]triazine-5-carboxamide, 4-amino-N-(4-(((((3,5-dimethylphenyl)amino)carbonyl)amino)phenyl)pyrrolo[2,1-f][2,1,4]triazine-5-carboxamide, 4-amino-N-(4-((((3-methylphenyl)amino)carbonyl)amino)phenyl)pyrrolo[2,1-f][2,1,4]triazine-5-carboxamide, 4-amino-N-(4-((((4-methylphenyl)amino)carbonyl)amino)phenyl)pyrrolo[2,1-f][2,1,4]triazine-5-carboxamide, 4-amino-N-(4-((((2-methylphenyl)amino)carbonyl)amino)phenyl)pyrrolo[2,1-f][2,1,4]triazine-5-carboxamide, 4-amino-N-(4-((((3-methoxyphenyl)amino)carbonyl)amino)phenyl)pyrrolo[2,1-f][2,1,4]triazine-5-carboxamide, 4-amino-N-(4-((((4-methoxyphenyl)amino)carbonyl)amino)phenyl)pyrrolo[2,1-f][2,1,4]triazine-5-carboxamide, 4-amino-N-(4-((((3-(trifluoromethyl)phenyl)amino)carbonyl)amino)phenyl)pyrrolo[2,1-f][2,1,4]triazine-5-carboxamide, 4-amino-N-(4-(((cyclopropylamino)carbonyl)amino)phenyl)pyrrolo[2,1-f][2,1,4]triazine-5-carboxamide, 4-amino-N-(4-(((cyclopentylamino)carbonyl)amino)phenyl)pyrrolo[2,1-f][2,1,4]triazine-5-carboxamide, 4-amino-N-(4-(((thien-3-ylamino)carbonyl)amino)phenyl)pyrrolo[2,1-f][2,1,4]triazine-5-carboxamide, 4-amino-N-(4-(((pyridin-3-ylamino)carbonyl)amino)phenyl)pyrrolo[2,1-f][2,1,4]triazine-5-carboxamide, 4-amino-N-(4-(benzoylamino)phenyl)pyrrolo[2,1-f][2,1,4]triazine-5-carboxamide, 4-amino-N-(4-((((2-fluoro-5-methylphenyl)amino)carbonyl)amino)phenyl)pyrrolo[2,1-f][2,1,4]triazine-5-carboxamide, 4-amino-N-(4-((((4-(2-hydroxyethyl)phenyl)amino)carbonyl)amino)phenyl)pyrrolo[2,1-f][2,1,4]triazine-5-carboxamide, 4-amino-N-(4-((((3-(2-hydroxyethyl)phenyl)amino)carbonyl)amino)phenyl)pyrrolo[2,1-f][2,1,4]triazine-5-carboxamide, 4-amino-N-(4-((((3-(hydroxymethyl)phenyl)amino)carbonyl)amino)phenyl)pyrrolo[2,1-f][2,1,4]triazine-5-carboxamide, 4-amino-N-(4-(((((3-(3-hydroxypropoxy)phenyl)amino)carbonyl)amino)phenyl)pyrrolo[2,1-f][2,1,4]triazine-5-carboxamide, 4-amino-N-(3-((anilinocarbonyl)amino)phenyl)pyrrolo[2,1-f][2,1,4]triazine-5-carboxamide, 4-amino-N-(3-(((((3-methylphenyl)amino)carbonyl)amino)phenyl)pyrrolo[2,1-f][2,1,4]triazine-5-carboxamide, 4-amino-N-(5-(2-((3-fluorophenyl)amino)-2-oxoethyl)-1,3-thiazol-2-yl)pyrrolo[2,1-f][2,1,4]triazine-5-carboxamide, 4-amino-N-(4-(((((3-(morpholin-4-ylmethyl)phenyl)amino)carbonyl)amino)phenyl)pyrrolo[2,1-f][2,1,4]triazine-5-carboxamide, 4-amino-N-(4-(((((3-methylphenyl)amino)carbonyl)amino)methyl)phenyl)pyrrolo[2,1-f][2,1,4]triazine-5-carboxamide, 4-amino-N-(4-(((((3-fluorophenyl)amino)carbonyl)amino)methyl)phenyl)pyrrolo[2,1-f][2,1,4]triazine-5-carboxamide, 4-amino-N-(3-(((((3-fluorophenyl)amino)carbonyl)amino)methyl)phenyl)pyrrolo[2,1-f][2,1,4]triazine-5-carboxamide, 4-amino-N-(3-(((anilinocarbonyl)amino)methyl)phenyl)pyrrolo[2,1-f][2,1,4]triazine-5-carboxamide 4-amino-N-(3-(((((4-(trifluoromethyl)phenyl)amino)carbonyl)amino)methyl)phenyl)pyrrolo[2,1-f][2,1,4]triazine-5-carboxamide;

4-amino-N-(3-(((((3,4-difluorophenyl)amino)carbonyl)amino)methyl)phenyl)pyrrolo[2,1-f][2,1,4]triazine-5-carboxamide;

4-amino-N-(3-(((((4-chloro-2-fluorophenyl)amino)carbonyl)amino)methyl)phenyl)pyrrolo[2,1-f][2,1,4]triazine-5-carboxamide;

4-amino-N-(3-(((((3-chlorophenyl)amino)carbonyl)amino)methyl)phenyl)pyrrolo[2,1-f][2,1,4]triazine-5-carboxamide;

4-amino-N-(3-(((((4-methylphenyl)amino)carbonyl)amino)methyl)phenyl)pyrrolo[2,1-f][2,1,4]triazine-5-carboxamide;

4-amino-N-(3-(((((4-chlorophenyl)amino)carbonyl)amino)methyl)phenyl)pyrrolo[2,1-f][2,1,4]triazine-5-carboxamide;

4-amino-N-(3-(((((4-fluorophenyl)amino)carbonyl)amino)methyl)phenyl)pyrrolo[2,1-f][2,1,4]triazine-5-carboxamide;

4-amino-N-(3-(((((pyridin-3-ylamino)carbonyl)amino)methyl)phenyl)pyrrolo[2,1-f][2,1,4]triazine-5-carboxamide;

4-amino-N-(3-(((((4-(difluoromethoxy)phenyl)amino)carbonyl)amino)methyl)phenyl)pyrrolo[2,1-f][2,1,4]triazine-5-carboxamide;

4-amino-N-(3-(((((2,4-difluorophenyl)amino)carbonyl)amino)methyl)phenyl)pyrrolo[2,1-f][2,1,4]triazine-5-carboxamide;

4-amino-N-(3-(((((2,5-difluorophenyl)amino)carbonyl)amino)methyl)phenyl)pyrrolo[2,1-f][2,1,4]triazine-5-carboxamide;

4-amino-N-(4-(((((4-chloro-2-fluorophenyl)amino)carbonyl)amino)phenyl)pyrrolo[2,1-f][2,1,4]triazine-5-carboxamide; and 4-amino-N-(4-((((4-(trifluoromethyl)phenyl)amino)carbonyl)amino)phenyl)pyrrolo[2,1-f][2,1,4]triazine-5-carboxamide.

9. A composition comprising an excipient and a therapeutically effective amount of a compound having Formula I of claim 1.

* * * * *